US008942063B2

(12) United States Patent
Vu et al.

(10) Patent No.: US 8,942,063 B2
(45) Date of Patent: Jan. 27, 2015

(54) DATA ACQUISITION AND PROCESSING SYSTEM AND METHOD FOR INVESTIGATING SUB-SURFACE FEATURES OF A ROCK FORMATION

(75) Inventors: Cung Khac Vu, Houston, TX (US); Kurt Nihei, Oakland, CA (US); Paul A. Johnson, Santa Fe, NM (US); Robert Guyer, Reno, NV (US); James A. Ten Cate, Los Alamos, NM (US); Pierre-Yves Le Bas, Los Alamos, NM (US); Caréne S. Larmat, Los Alamos, NM (US)

(73) Assignees: Chevron U.S.A Inc., San Ramon, CA (US); Los Alamos National Security, LLC, Los Alamos, NM (US)

( * ) Notice: Subject to any disclaimer, the term of this patent is extended or adjusted under 35 U.S.C. 154(b) by 619 days.

(21) Appl. No.: 13/292,924

(22) Filed: Nov. 9, 2011

(65) Prior Publication Data

US 2012/0120767 A1    May 17, 2012

Related U.S. Application Data

(60) Provisional application No. 61/413,173, filed on Nov. 12, 2010.

(51) Int. Cl.
*G01V 1/44* (2006.01)
*G01V 1/50* (2006.01)
(Continued)

(52) U.S. Cl.
CPC . *G01V 1/006* (2013.01); *G01V 1/44* (2013.01); *G01V 1/52* (2013.01); *G01V 1/46* (2013.01);
(Continued)

(58) Field of Classification Search
CPC .............. G01V 1/44; G01V 1/48; G01V 1/50
USPC .................................. 367/25, 31, 23
See application file for complete search history.

(56) References Cited

U.S. PATENT DOCUMENTS 3,302,745 A    2/1967   Ikrath
3,521,154 A    7/1970   Maricelli
(Continued)

FOREIGN PATENT DOCUMENTS

EP    519810 A1    12/1992
EP    1122558 A    8/2001
(Continued)

OTHER PUBLICATIONS

U.S. Notice of Allowance dated Aug. 18, 20014 for U.S. Appl. No. 13/292,915.
(Continued)

*Primary Examiner* — Ian J Lobo
(74) *Attorney, Agent, or Firm* — Pillsbury Winthrop Shaw Pittman, LLP

(57) ABSTRACT

A system and a method includes generating a first signal at a first frequency; and a second signal at a second frequency. Respective sources are positioned within the borehole and controllable such that the signals intersect in an intersection volume outside the borehole. A receiver detects a difference signal returning to the borehole generated by a non-linear mixing process within the intersection volume, and records the detected signal and stores the detected signal in a storage device and records measurement parameters including a position of the first acoustic source, a position of the second acoustic source, a position of the receiver, elevation angle and azimuth angle of the first acoustic signal and elevation angle and azimuth angle of the second acoustic signal.

43 Claims, 27 Drawing Sheets

(51) Int. Cl.
  *G01V 1/00* (2006.01)
  *G01V 1/46* (2006.01)
  *G01V 1/52* (2006.01)
  *G10K 15/02* (2006.01)

(52) U.S. Cl.
  CPC .......... *G10K 15/02* (2013.01); *G01V 2210/127* (2013.01); *G01V 2210/588* (2013.01); *G01V 2210/125* (2013.01)
  USPC .......................................... 367/32; 367/25

(56) References Cited

U.S. PATENT DOCUMENTS

| | | | |
|---|---|---|---|
| 3,732,945 | A | 5/1973 | Lavigne |
| 3,872,421 | A | 3/1975 | Rogers et al. |
| 3,974,476 | A | 8/1976 | Cowles |
| 4,253,166 | A | 2/1981 | Johnson |
| 4,382,290 | A | 5/1983 | Havira |
| 4,509,149 | A | 4/1985 | Ruehle |
| 4,606,014 | A | 8/1986 | Winbow et al. |
| 4,646,565 | A | 3/1987 | Siegfried |
| 4,757,873 | A | 7/1988 | Linyaev et al. |
| 4,805,873 | A | 2/1989 | Mouton |
| 5,144,590 | A | 9/1992 | Chon |
| 5,521,882 | A | 5/1996 | D'Angelo et al. |
| 5,719,823 | A | 2/1998 | Earp |
| 6,009,043 | A | 12/1999 | Chon et al. |
| 6,175,536 | B1 | 1/2001 | Khan |
| 6,216,540 | B1 | 4/2001 | Nelson et al. |
| 6,289,284 | B1 | 9/2001 | Yamamoto |
| 6,440,075 | B1 | 8/2002 | Averkiou |
| 6,597,632 | B2 | 7/2003 | Khan |
| 6,631,783 | B2 | 10/2003 | Khan |
| 6,704,247 | B1 | 3/2004 | Ruffa |
| 6,937,938 | B2 | 8/2005 | Sansone |
| 7,059,404 | B2 | 6/2006 | Flecker et al. |
| 7,301,852 | B2 | 11/2007 | Leggett, III et al. |
| 7,310,580 | B2 | 12/2007 | Zhou et al. |
| 7,463,551 | B2 | 12/2008 | Leggett, III et al. |
| 7,535,795 | B2 | 5/2009 | Varsamis et al. |
| 7,710,822 | B2 | 5/2010 | Harmon |
| 8,116,167 | B2 | 2/2012 | Johnson et al. |
| 8,576,659 | B2 | 11/2013 | Egerev et al. |
| 2004/0095847 | A1 | 5/2004 | Hassan et al. |
| 2005/0036403 | A1 | 2/2005 | Leggett et al. |
| 2010/0002540 | A1 | 1/2010 | Vu et al. |
| 2010/0265794 | A1 | 10/2010 | Johnson et al. |
| 2010/0284250 | A1* | 11/2010 | Cornish et al. ............. 367/124 |

FOREIGN PATENT DOCUMENTS

| | | |
|---|---|---|
| GB | 2168568 | 6/1986 |
| GB | 2404983 A | 2/2005 |
| SU | 913303 | 3/1982 |
| WO | 0194983 A2 | 12/2001 |
| WO | WO 02/04985 A2 | 1/2002 |
| WO | WO 2007/030016 | 3/2007 |
| WO | WO 2008/094050 A2 | 8/2008 |

OTHER PUBLICATIONS

Mexican Office Action dated Jun. 5, 2014 for Appln. No. MX/A/2013/005333.
Australian Examination Report dated Feb. 7, 2014 for 2011326567.
International Search Report adn Written Opinion of PCT/US2011/059967, mailed Mar. 21, 2013, 20 pages.
International Search Report and Written Opinion for PCT/US2011/059973, mailed Feb. 14, 2013, 13 pages.
Peter J. Westervelt; "Parametric Acoustic Array", The Journal of the Acoustical Society of America, vol. 35, No. 4, Apr. 1963, pp. 535-537.
International Search Report and Written Opinion for PCT International Patent Application No. PCT/US2009/047934, mailed Jan. 12, 2009.
Johnson et al., "Nonlinear Generation of Elastic waves in Crystalline Rock", Journal of Geophysical Research, vol. 92, No. B5, pp. 3597-3602, Apr. 10, 1987.
International Search Report and Written Opinion for PCT International Patent Application No. PCT/US2009/047184, mailed Dec. 21, 2009.
International Preliminary Report on Patentability for PCT International Patent Application No. PCT/US2009/047184, mailed Dec. 23, 2010.
International Search Report and Written Opinion for PCT International Patent Application No. PCT/US2010/031485, mailed Aug. 2, 2010.
International Search Report and Written Opinion for PCT International Patent Application No. PCT/US2010/031490, mailed Sep. 14, 2010.
Aas et al.; 3-D Acoustic Scanner, SPE, Society of Petroleum Engineers, Sep. 23-26, 1990, pp. 725-732.
Ostrovsky. L.A., and Johnson, P.A., "Dynamic Nonlinear Elasticity in Geomaterials", Rivista del Nuovo Cimento, vol. 24, No. 7., 2001.
Johnson, Paul A., and Shankland, Thomas J., "Nonlinear Generation of Elastic Waves in Granite and Sandstone: Continuous Wave and Travel Time Observations", Journal of Geophysical Research, vol. 94, No. B12, 1989, pp. 17,729-17,733.
Jones, G.L. and Kobett, D.R., "Interaction of Elastic Waves in an Isotropic Solid", The Journal of the Acoustical Society of America, vol. 35, No. 1, 1963, pp. 5-10.
Rollins, F.R., Taylor, L.H. and Todd, P.H., "Ultrasonic Study of Three-Phonon Interactions. II. Experimental Results", Physical Review, vol. 136, No. 3A, 1964, pp. 597-601.
Korneev, Valeri A., Nihei, Kurt T. and Myer, Larry R., "Nonlinear Interaction of Plane Elastic Waves", Lawrence Berkeley National Laboratory Report LBNL-41914, 1998.
International Preliminary Report on Patentability for PCT International Patent Application No. PCT/US2010/031490, mailed Oct. 27, 2011.
International Preliminary Report on Patentability for PCT International Patent Application No. PCT/US2010/031485, mailed Oct. 27, 2011.
Tserkovnyak et al.; "Non-linear tube waves in permeable formations: Difference frequency generation", Journal of the Acoustical Society of America, Jul. 1, 2004, vol. 116, Issue 1, pp. 209-216.
Singapore Office Action for Appln. No. 201009640-2, mailed Dec. 2, 2011.
PCT International Search Report and Written Opinion for PCT International Patent Application No. PCT/US2011/035608, mailed Dec. 22, 2011.
PCT International Search Report and Written Opinion for PCT International Patent Application No. PCT/US2011/035595, mailed Dec. 27, 2011.
PCT International Search Report and Written Opinion for PCT International Patent Application No. PCT/US2011/035358, mailed Dec. 29, 2011.
International Preliminary Report on Patentability for PCT International Patent Application No. PCT/US2009/047934, mailed Jan. 13, 2011.
International Preliminary Report on Patentability for PCT International Patent Application No. PCT/US2009/047184, mailed Dec. 14, 2010.
International Preliminary Report on Patentability for PCT International Patent Application No. PCT/US2009/047934, mailed Dec. 1, 2009.
U.S. Office Action dated Aug. 25, 2014 for U.S. Appl. No. 13/292,908.
Australian Office Action dated. Aug. 28, 2014 for Appln. No. 2011326570.
Mexican Office Action dated Sep. 25, 2014 for Appln. No. MX/A/2014/005694.
U.S. Office Action dated Nov. 26, 2014 for U.S. Appl. No. 13/292,941.

* cited by examiner

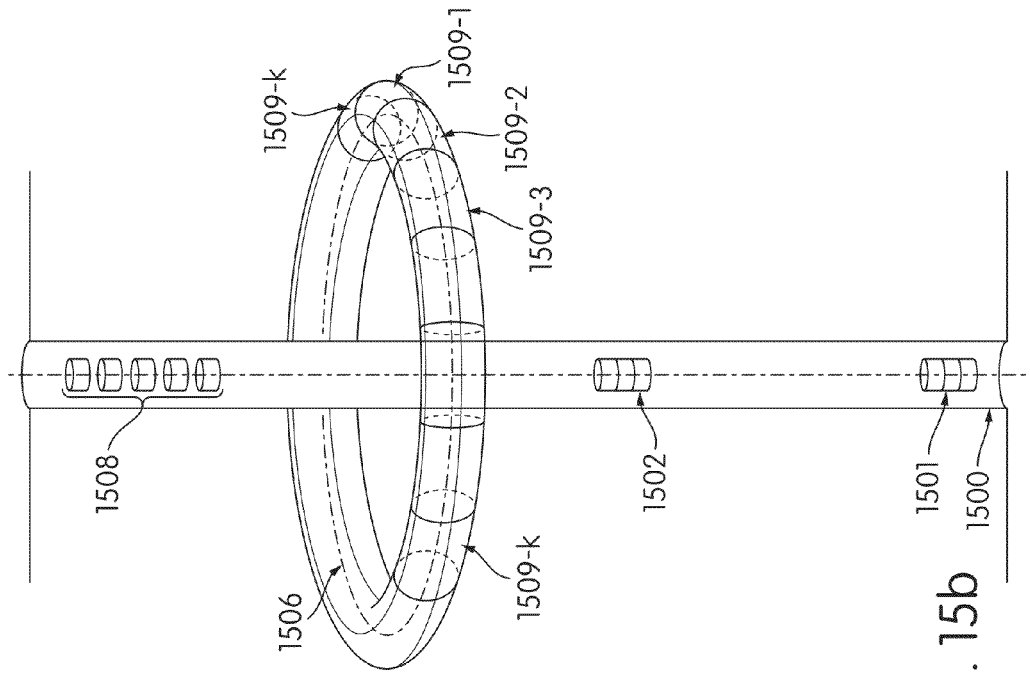
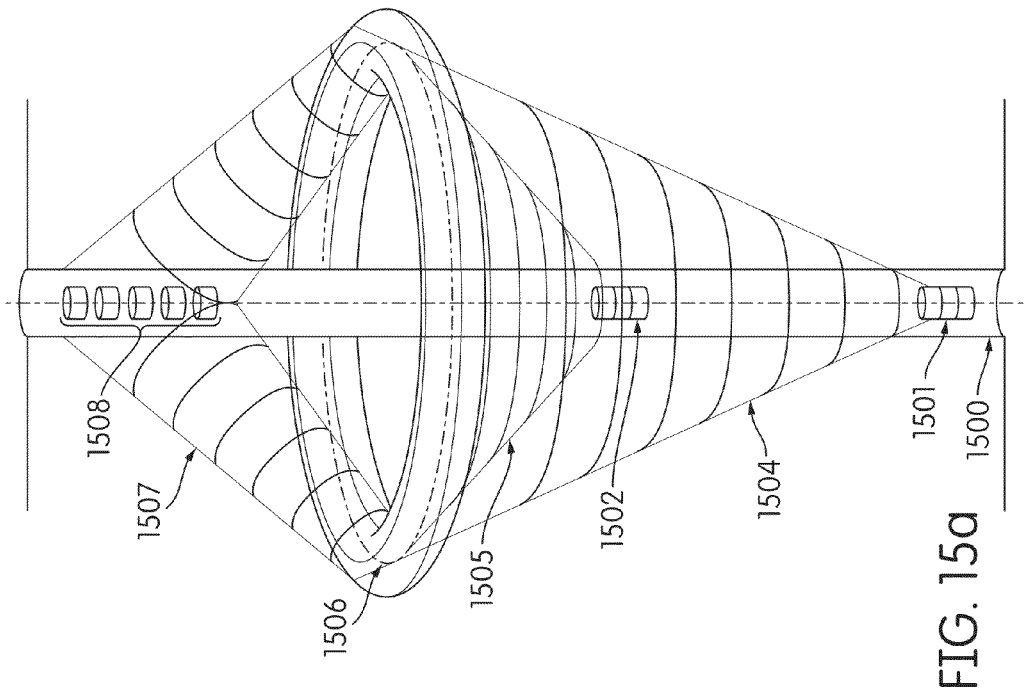
FIG. 15a
FIG. 15b

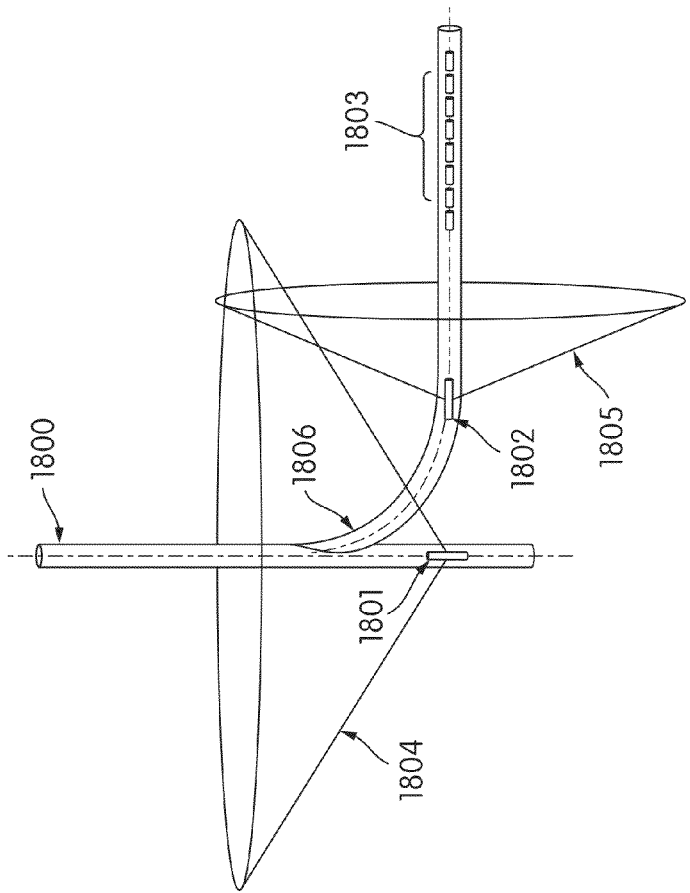
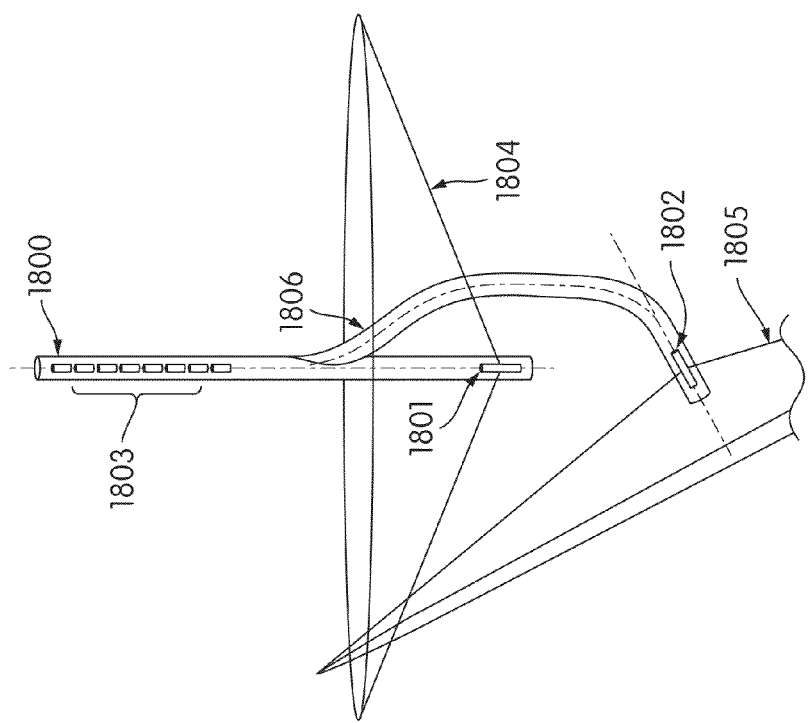
FIG. 18b
FIG. 18a

DATA ACQUISITION AND PROCESSING SYSTEM AND METHOD FOR INVESTIGATING SUB-SURFACE FEATURES OF A ROCK FORMATION

CROSS REFERENCE TO RELATED APPLICATION

This application claims the benefit of U.S. patent application Ser. No. 61/413,173, filed on Nov. 12, 2010, the entire contents of which is incorporated herein by reference.

GOVERNMENT RIGHTS

This invention was made with Government support under Cooperative Research and Development Agreement (CRADA) Contract Number DE-AC52-06NA25396 awarded by the United States Department of Energy. The Government may have certain rights in this invention.

FIELD

The present invention relates generally to seismic interrogation of rock formations and more particularly to creating three-dimensional images of non-linear properties and/or the compressional to shear velocity ratio in a region remote from a borehole using a combination of sources in a borehole, and receiving and analyzing a resultant third wave formed by a mixing process.

BACKGROUND

Acoustic interrogation of subsurface features tends to be limited by the size and power of practical sources, and in practice, the output of down hole acoustic transducers is limited by the power transmission capabilities of the wireline cable. High frequency signals have a relatively short penetration distance, while low frequency signals generally require large sources, clamped to the borehole wall, to maximize energy transfer to the formation and minimize unwanted signals within the well bore. Currently, acoustic borehole tools are designed with acoustic sources in the borehole to detect returning acoustic waves that are propagating along the borehole walls or scattered by inhomogeneities of linear properties of rock formations surrounding the borehole. U.S. Pat. No. 7,301,852 to Leggett, III et al. discloses a Logging While Drilling tool, designed to detect rock formation boundaries. The tool uses two acoustic source arrays emitting two acoustic waves from a borehole that generate a third wave by non-linear mixing in the rock formation surrounding the borehole at the location of intersection of the acoustic waves. The third wave continues forward and interacts linearly with heterogeneities in the subsurface properties. The third wave is scattered by the heterogeneities in the subsurface properties, and the scattered signal is detected by sensors in the logging tool. U.S. Pat. No. 7,301,852 does not discuss detecting the third wave directly but rather the signal that is scattered by the heterogeneities in the rock formation. U.S. Pat. No. 7,301,852 merely uses the resultant scattered wave to detect rock formation boundaries.

Attempts have been made to characterize the non-linear properties of a formation in the area of oil and gas prospecting from boreholes, but each has its own limitations. For example, U.S. Pat. No. 5,521,882 to D'Angelo et al. discloses an acoustic tool designed to record with pressure receivers non-linear waves generated by non-linear mixing of two waves. The non-linear waves propagate along the borehole wall with limited penetration into the surrounding rock formation and refract back into the well bore fluid. The indication of non-linearity is utilized to provide an indication of the relative consolidation of the formation surrounding the borehole. U.S. Pat. No. 5,521,882 does not discuss measuring non-linear characteristics of a rock formation away from the borehole. U.S. Pat. No. 6,175,536 by Khan discloses a method to estimate the degree of non-linearity of earth formations from spectral analysis of seismic signals transmitted into the earth formations from a first borehole and received in a second borehole. The method in U.S. Pat. No. 6,175,536 determines from the spectral analysis the presence of a frequency at a receiver located at the second borehole representing a sum or a difference of two selected frequencies of the transmitted seismic signals generated by two sources located at the first borehole. U.S. Pat. No. 6,175,536 does not discuss measuring non-linear characteristics of a rock formation in a remote region of a borehole where the receiver and the sources are located in one borehole.

In light of these prior attempts, there is a need for a system and method for characterizing non-linear properties in a remote region from a borehole.

SUMMARY

An aspect of the present disclosure is to provide a system for investigating a rock formation outside a borehole. The system includes a first acoustic source configured to generate a first acoustic signal at a first frequency; and a second acoustic source configured to generate a second acoustic signal at a second frequency. The first acoustic source and the second acoustic source are arranged and positioned within the borehole and are controllable such that the first and the second acoustic signals intersect in an intersection volume outside the borehole and a start time difference is provided between the second acoustic signal and the first acoustic signal. The system also includes a receiver arranged within the borehole, the receiver being configured to receive a detected signal returning to the borehole having a frequency equal to a difference between the first frequency and the second frequency, the detected signal being generated by a non-linear mixing process from the first acoustic signal and the second acoustic signal in a non-linear mixing zone within the intersection volume. The system further includes a recording system configured to record the detected signal and store the detected signal in a storage device and to record measurement parameters including a position of the first acoustic source, a position of the second acoustic source, a position of the receiver, elevation angle and azimuth angle of the first acoustic signal and elevation angle and azimuth angle of the second acoustic signal.

Another aspect of the present disclosure is to provide a method of investigating a rock formation outside a borehole. The method includes generating, by a first acoustic source, a first signal at a first frequency; and generating, by a second acoustic source, a second signal at a second frequency. The first acoustic source and the second acoustic source are arranged and positioned within the borehole and are controllable such that the first and the second acoustic signals intersect in an intersection volume outside the borehole and a start time difference is provided between the second acoustic signal and the first acoustic signal. The method also includes receiving, by a receiver, a detected signal returning to the borehole having a frequency equal to a difference between the first frequency and the second frequency, the detected signal being generated by a non-linear mixing process from the first acoustic signal and the second acoustic signal in a non-linear mixing zone within the intersection volume. The method further includes recording the detected signal and storing the detected signal in a storage device and recording measurement parameters including a position of the first acoustic source, a position of the second acoustic source, a position of the receiver, elevation angle and azimuth angle of the first acoustic signal and elevation angle and azimuth angle of the second acoustic signal.

These and other objects, features, and characteristics of the present invention, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various Figures. It is to be expressly understood, however, that the drawings are for the purpose of illustration and description only and are not intended as a definition of the limits of the invention. As used in the specification and in the claims, the singular form of "a", "an", and "the" include plural referents unless the context clearly dictates otherwise.

BRIEF DESCRIPTION OF THE DRAWINGS

FIG. 9b shows a vector representation of the non-collinear acoustic mixing of FIG. 9a;

FIGS. 15a and 15b show an example non-collinear mixing arrangement in a toroid around the borehole at intersection of two coaxial cones, in accordance with aspects of the present disclosure;

FIG. 18a shows an example of a vertical well and sidetrack with receivers in the vertical part of the well, in accordance with aspects of the present disclosure;

FIG. 18b shows another example of a vertical pilot hole and horizontal sidetrack with receivers in the sidetrack, in accordance with aspects of the present disclosure.

DETAILED DESCRIPTION

Figure 1:
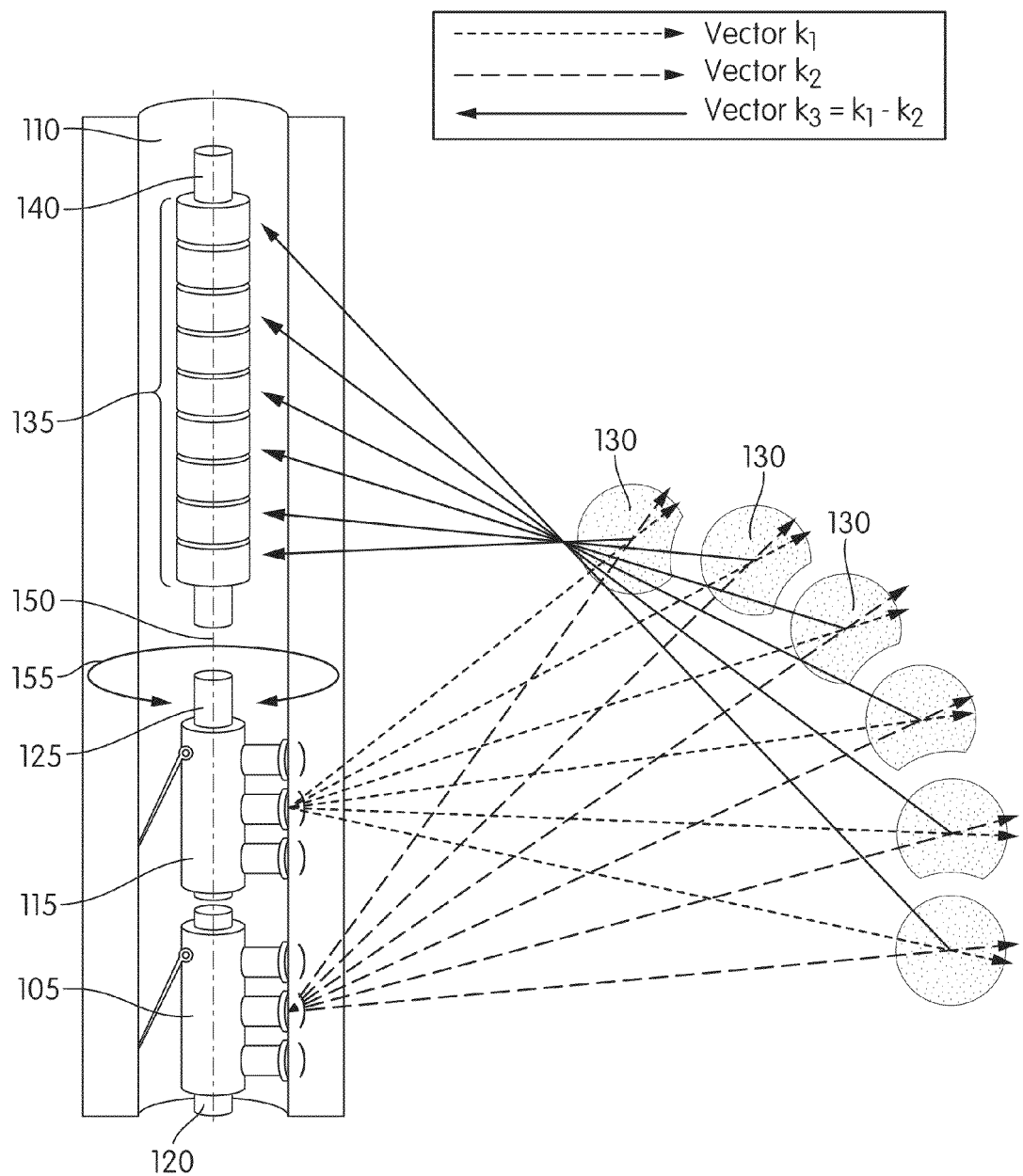
FIG. 1 shows a configuration for creating three-dimensional images of non-linear properties in a region remote from a borehole, in accordance with various aspects of the disclosure.

FIG. 1 shows one of several possible configurations for creating three-dimensional images of non-linear properties and the compressional to shear velocity ratio in a region remote from a borehole in accordance with various aspects of the disclosure. First acoustic source 105 is arranged in borehole 110 to generate a steerable primary beam of acoustic energy at a first frequency $f_1$. Second acoustic source 115 is also arranged in borehole 110 to generate a steerable primary beam of acoustic energy at a second frequency $f_2$. By way of a non-limiting example, both first acoustic source 105 and second acoustic source 115 may be a phased array of sources and may be configured to generate either compressional or shear steerable beams. In the present disclosure, the term "acoustic" can refer to P, SV or SH acoustic mode.

As shown in FIG. 1, first acoustic source 105 is arranged on first tool body 120 and second acoustic source 115 is arranged on second tool body 125. However, the disclosure is not so limiting as first tool body 120 and second tool body 125 may also be arranged together on a common tool body (not shown). Tool bodies 120 and 125 are arranged to be independently moveable within bore hole 110 in at least two degrees of freedom including translation along the longitudinal axis 150 of borehole 110 and rotation 155 in azimuth about the longitudinal axis of borehole 110. First acoustic source 105 may be arranged above or below second acoustic source 115 in borehole 110. Tool bodies 120 and 125 may be arranged on a conveyed logging tool (not shown) within borehole 110.

For a given azimuth orientation of first acoustic source 105 and second acoustic source 115, the beam generated by second acoustic source 115 and the beam generated by first acoustic source 105 are configured such that the beams converge and intercept in mixing zones 130 remote from borehole 110. By a combination of independently steering the beams and changing the separation between the sources 105, 115, the mixing zones 130 move in a plane defined by the beams and the longitudinal borehole axis 150, while controlling the angle of interception. The distance of mixing zones 130 from borehole 110 can range from near the edge of borehole 110 to about 300 meters into the surrounding subsurface rock formation. By way of a non-limiting example, the phase difference and/or start time differences between adjacent elements in the source array 105, 115 referred to in the above paragraphs may be modified to focus the acoustic energy of the primary beams at a particular mixing zone 130.

The non-linear properties of the earth at the location between the two waves result in the generation of a third elastic wave. The third elastic wave is a result of a three-wave mixing process that occurs in nonlinear materials, in this case, rock formations. In this process, two converging non-collinear waves of different frequencies, $f_1$, and $f_2$, also called primary waves, mix to form additional waves at the harmonic and intermodulation frequencies $f_1-f_2$, $f_1+f_2$, $2 \times f_1$ and $2 \times f_2$, etc. The strength of the third wave is a function the non-linearity of the rocks in the mixing zones. By way of a non-limiting example, when a primary compressional (P) wave with a frequency $f_1$ and a primary shear (SV) wave with a frequency $f_2$ cross or intersect in a non-linear medium, a third compressional (P) or shear (SV) wave is generated with a frequency $f_1-f_2$.

Under propagation selection rules, the third wave propagation vector is co-planar with the propagation vectors of the two primary waves. Certain combinations of angle of intersection, $f_1/f_2$ ratio and compressional to shear velocity ratio result in a third elastic wave with frequency $f_1-f_2$ propagating in a specific angle relative to the primary beams back to the borehole 110.

Sensor or receiver array 135 is arranged at a specific location in borehole 110 to detect the third wave returning to the borehole 110. In one embodiment, as shown for example in the FIG. 1, sensor array 135 comprises more than one sensor, arranged as an array of sensors on sensor tool body 140 and separate from tool bodies 120 and 125. Sensor 135 is configured to be independently moveable within bore hole 110 along the longitudinal axis 150 of borehole 110. For example, sensor tool body 140 can be arranged below tool bodies 120 and 125 or arranged above and below tool bodies 120 and 125. In some embodiments, sensor tool body 140 can be connected to either or both tool bodies 120 and 125.

Figure 2:
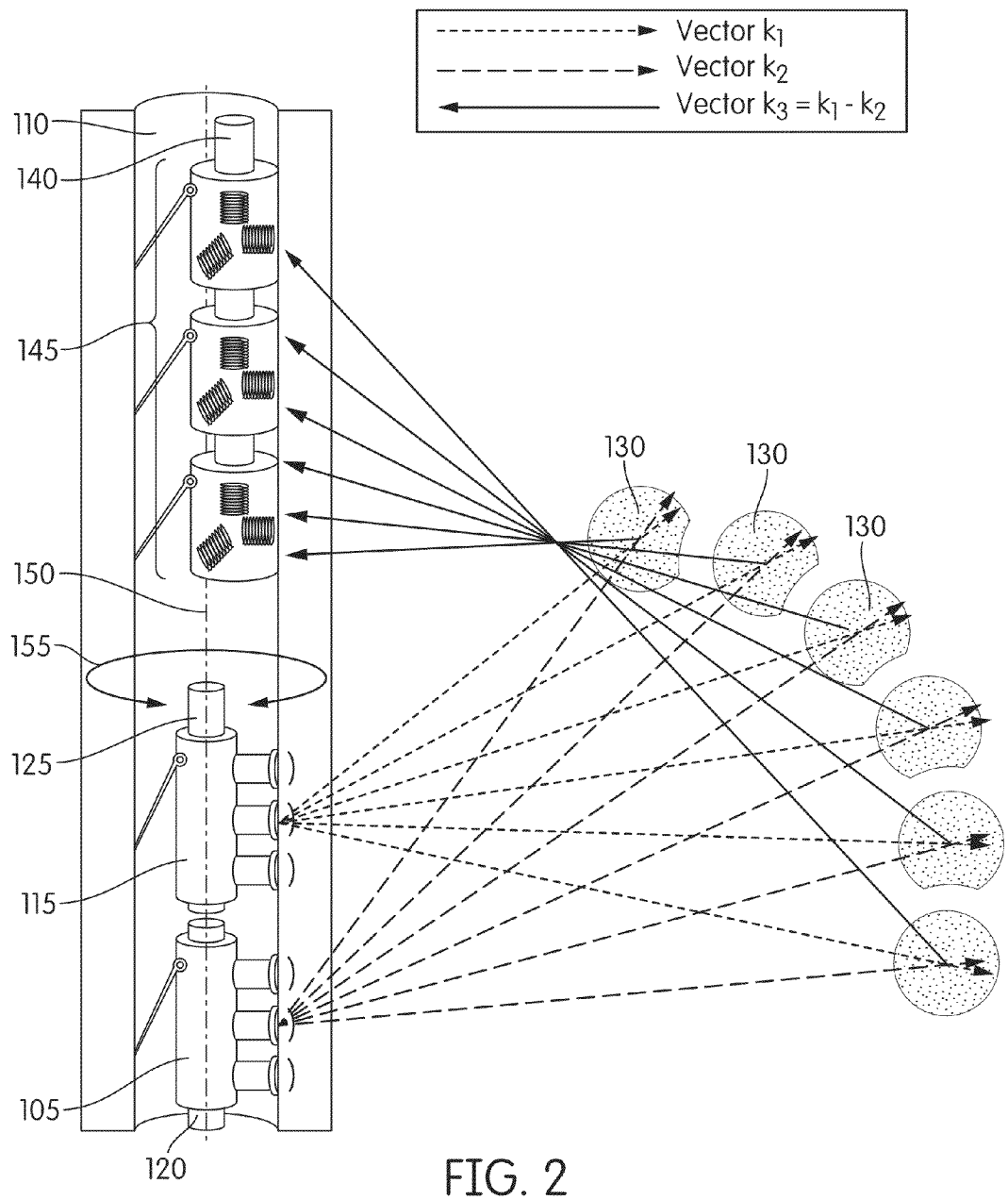
FIG. 2 shows another configuration for creating three-dimensional images of non-linear properties in a region remote from a borehole, in accordance with aspects of the disclosure.

The third wave is detected at borehole 110 by sensor array 135. FIG. 2 shows an arrangement similar to FIG. 1, wherein receiver 135 includes three component geophone 145 clamped to the borehole walls. The resultant signal is decomposed by processing into its elevation and azimuth in order to add redundancy to the system by determining the direction of the incoming third wave arrival.

In one embodiment, a first processor or controller can be provided and configured to execute machine-readable instructions (not shown) to perform various processing tasks, such as controlling source firing and compressing or filtering the data recorded by sensor array 135. In one embodiment, the first processor can be arranged within the borehole 110. In one embodiment, a second processor can be provided and configured to execute machine-readable instructions (not shown) to assist the first processor or perform different processing tasks than the first processor. For example, the second processor may perform part or all processing activities in creating the three-dimensional images. A transmitter or transceiver (not shown) may be arranged in borehole 110 to transmit data up-hole through a wireline cable (not shown). In one embodiment, the second processor can be, for example, arranged outside the borehole.

At a given depth along the borehole of one of the sources 105, 115, sweeping the beams in elevation at constant relative bearing to spatially scan the mixing zone in a plane passing through the borehole axis, rotating the sources azimuthally to rotationally scan the mixing region and moving the whole assembly along borehole 110, results in scanning a 3D volume of mixing zones around the borehole for non-linear properties. With sources 105, 115 and sensor array 135 located on independent tool bodies, redundancy in the data can be obtained and the depth of investigation can be varied. In this way, a 3D volume of the rocks surrounding the borehole can be interrogated for non-linear properties and a 3D image of non-linear properties can be processed and computed from the returned signals, i.e., signals detected by sensor array 135.

Figure 3:
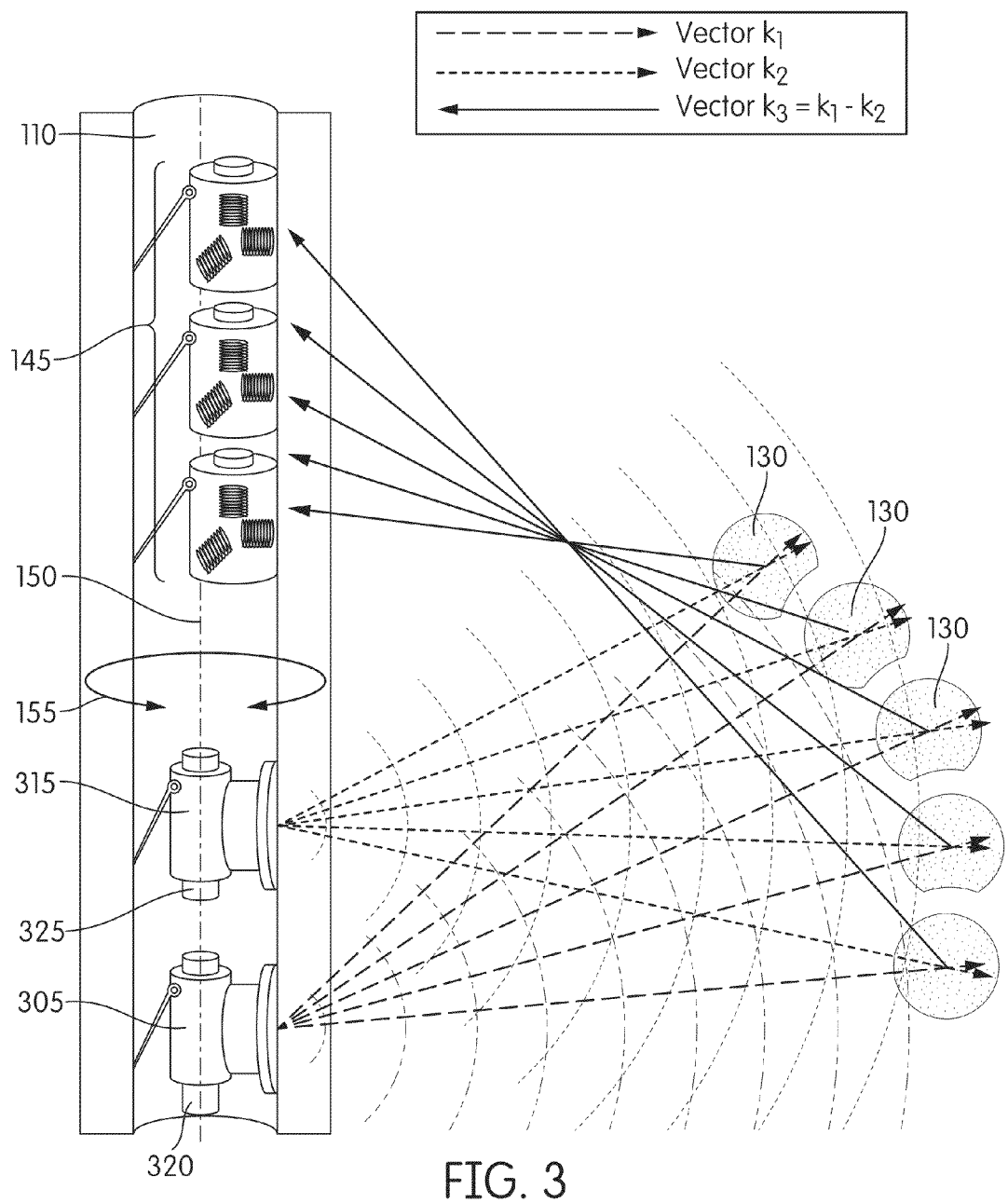
FIG. 3 shows yet another configuration for creating three-dimensional images of non-linear properties in a region remote from a borehole, in accordance with aspects of the disclosure.

FIG. 3 shows another arrangement for creating three-dimensional images of non-linear properties in a region remote from borehole 110 in accordance with another embodiment of the present invention. The arrangement of FIG. 3 is similar to the arrangement in FIG. 2, with the primary difference being that the sources are arranged in borehole 110 to produce elastic waves (e.g., spherical waves) instead of steerable directional beams. With reference to FIG. 3, first acoustic source 305 is arranged in borehole 110 on first tool body 320 to generate a first elastic wave of acoustic energy at a first frequency $f_1$. Second acoustic source 315 is arranged in borehole 110 on second tool body 325 to generate a second elastic wave of acoustic energy at a second frequency $f_2$. First and second elastic waves produced by sources 305, 315 are arranged to intersect away from borehole 110 at various mixing zones 130. Receiver 145 is arranged within borehole 110 to receive a third wave that is produced in the mixing zones 130 by the three-wave mixing process discussed above, and further discussed below. Since the waves produced by sources 305, 315 are essentially non-directional, mixing between the waves occurs simultaneously in the entire area of mixing zones 130, that also extends out of the plane of the Figure, and receiver 145 tends to have directional characteristics. By way of a non-limiting example, a three component geophone array may be used for this purpose. The resultant signal is decomposed by processing into multiple arrival signals at a range of elevations and azimuths and travel times. Given the locations of sources 305 and 315 and the receivers 145, the travel times and directions of each decomposed directional arrival, there is sufficient information to apply selection rules described in the following paragraphs to determine a unique mixing zone where the third wave was generated. This unique mapping allows the construction of a three dimensional (3D) image from the properties of the received signal.

Figure 4:
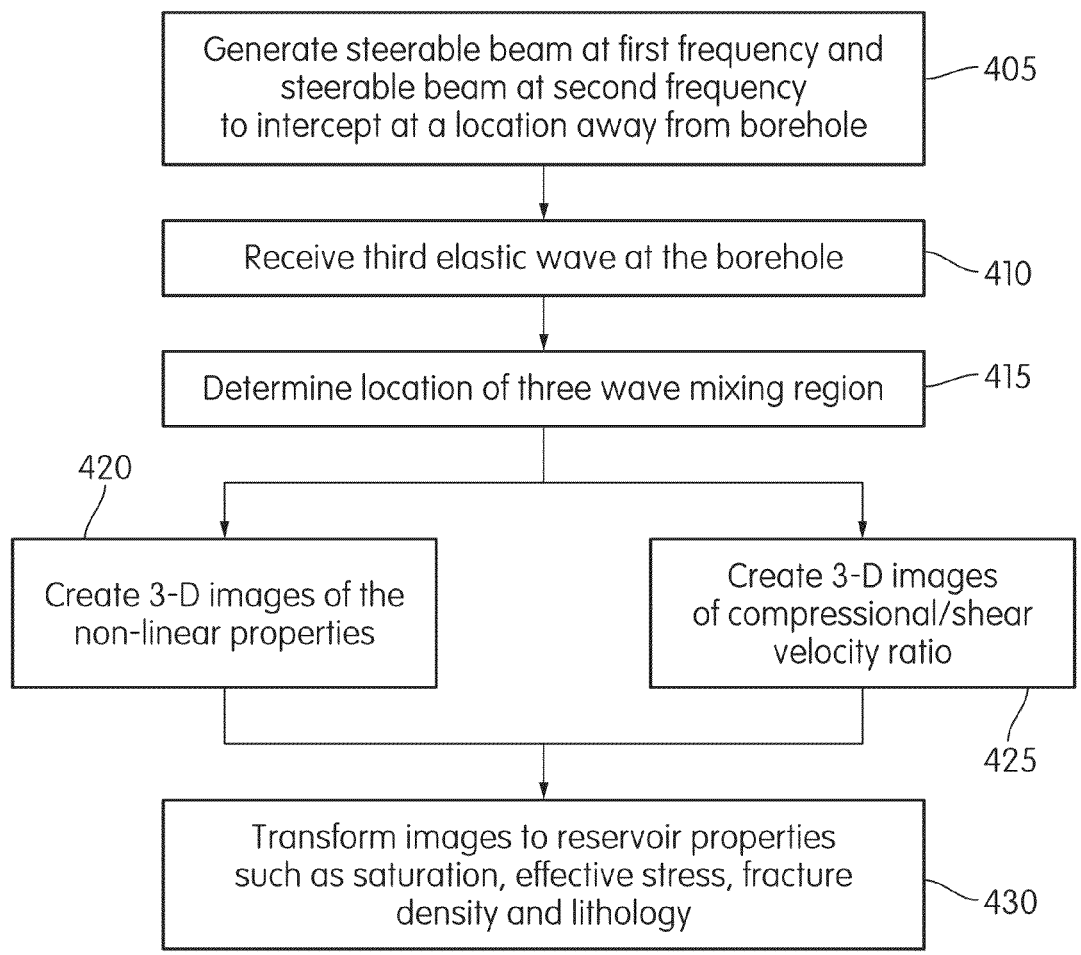
FIG. 4 shows a flow chart for creating three-dimensional images of non-linear properties in a region remote from a borehole, in accordance with various aspects of the disclosure.

FIG. 4 shows a flow chart for a method of creating three-dimensional images of non-linear properties and the compressional to shear velocity ratio in a region remote from a borehole using a conveyed logging tool, according to an embodiment of the present invention. The method begins at 405 where a first acoustic source is arranged in the borehole to generate a steerable beam elastic energy at a first frequency and a second acoustic source is arranged in the borehole to generate a steerable beam of elastic energy at a second frequency. The steerable beams at the first and second frequency are arranged to intersect at a location away from the borehole. As such, the second beam is generated at the same azimuth as the first beam, but at a different elevation relative to the longitudinal axis of the borehole. The method continues at 410 where a third elastic wave is received at the borehole by a sensor array. As discussed above, the third elastic wave is created by a mixing process, with a frequency equal to a difference between the first and second frequencies and a direction of propagation towards the borehole. At 415, a mixing location away from the borehole is determined from the arrangement of the first and second acoustic sources and properties of the third wave, by recourse to the selection rules. At 420, three-dimensional images are created of the non-linear properties using data recorded by repeating the generating of step 405, the receiving of step 410 and the determining of step 415 at a plurality of azimuths, elevations and longitudinal locations within the borehole. In cases of compressional-shear interaction, the received signals are analyzed in step 425 for the compressional/shear velocity (Vp/Vs) ratio as discussed in the above paragraphs. At 430, the non-linear properties are transformed to physical reservoir properties such as fluid saturation, effective stress, fracture density and mineralogy.

In some aspects of the present disclosure, the first and second acoustic sources may be beam or cylindrical, or spherical wave sources, and the sensor array may be any combination of non-directional single component sensors and three component geophones. Alternative permutations of the component parts offer different degrees of redundancy in signal processing and imaging.

In the special case where a primary compressional (P) wave with a frequency $f_1$ and a primary shear (S) wave with a frequency $f_2$ cross each other, in a non-linear medium, a third P or S wave is generated with the frequency $f_1-f_2$. If the primary P and S waves are beams with wave vectors $k_1$ and $k_2$, respectively, and the non-linear formation property is uniform, the kinematics of wave interaction requires the resulting third wave to be a plane wave with wave vector $k_3$ that obeys the selection rule $k_1-k_2=k_3$. The selection rule imposes a very tight restriction on the permissible crossing angles for the primary waves and a specific propagation direction of the third wave. The general kinematic theory for non-linear mixing of two linear plane waves and the selection rules and amplitude responses have contributions from Jones and Kobett (1963), Rollins, Taylor et al. (1964) and later by Korneev, Nihei and Myer (1998), all of which are hereby incorporated by reference in their entirety, who also provide specific relationships between non-linear parameters of the mixing medium and the non-linear mixing signal strength. For example, Equation 53 and 54 of Korneev, Nihei and Myer show that the mixing strength of P and SV (vertically polarized shear) plane waves is proportional to a specific combination of non-linear parameters of the rocks.

The selection rules governing the nonlinear interaction of two elastic plane waves can be used as guidance for the interaction of two elastic beams. These plane wave selection rules dictate that the following six nonlinear interactions produce backscattered waves.

TABLE 1

Selection Rules Governing Non-Linear Interaction of Two Elastic Plane Waves. In this table, and elsewhere in this document, $f_1$ is greater than $f_2$.

| Selection Rules | 1$^{st}$ beam or wave | 2$^{nd}$ beam or wave | Resultant 3$^{rd}$ beam or wave from 1$^{st}$ + 2$^{nd}$ |
|---|---|---|---|
| 1 | $P(f_1)$ | $SV(f_2)$ | $P(f_1 - f_2)$ |
| 2 | $P(f_1)$ | $SV(f_2)$ | $SV(f_1 - f_2)$ |
| 3 | $P(f_1)$ | $SH(f_2)$ | $SH(f_1 - f_2)$ |
| 4 | $P(f_1)$ | $SV(f_2)$ | $P(f_1 + f_2)$ |
| 5 | $SV(f_1)$ | $SV(f_2)$ | $P(f_1 + f_2)$ |
| 6 | $SH(f_1)$ | $SH(f_2)$ | $P(f_1 + f_2)$ |

Figure 5B:
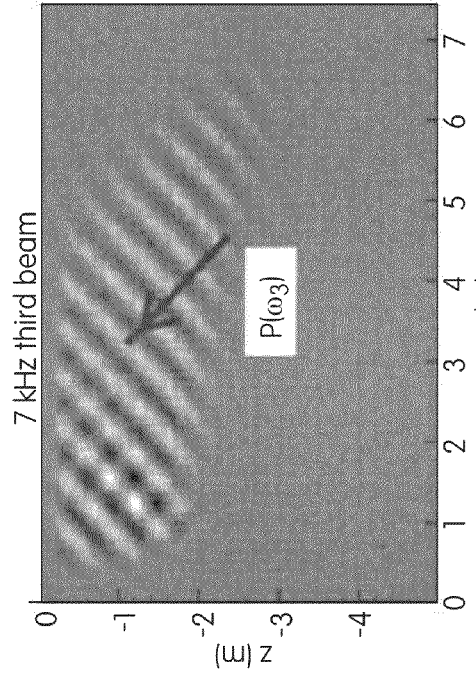
FIGS. 5a, 5b and 5c shows a numerical simulation of the first selection rule for a beam-beam interaction listed in Table 1 when the two primary waves are beams.
Figure 5A:
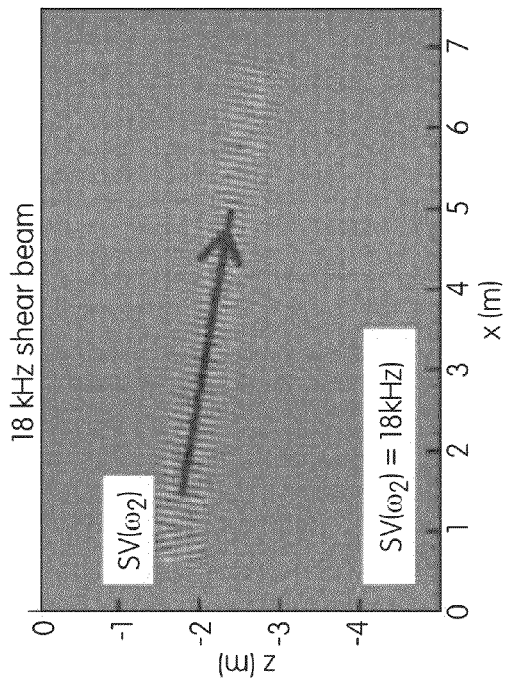
Figure 5C:
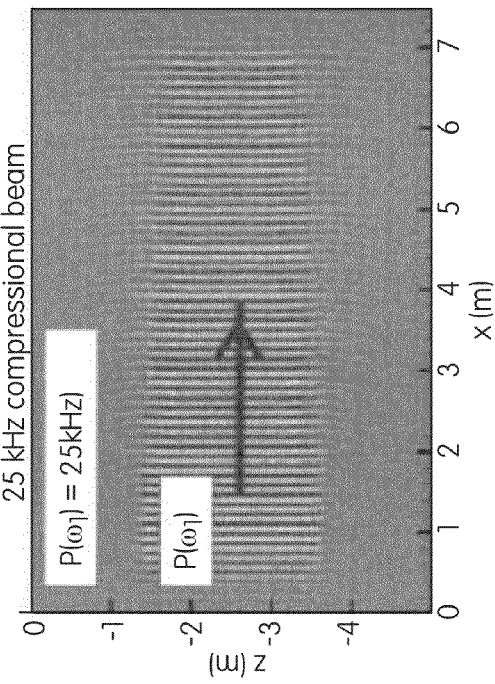

FIGS. 5a, 5b and 5c shows a numerical simulation of selection rule 1 of Table 1 when the two primary waves are beams of a beam-beam interaction. A 25 kHz compressional beam, shown in FIG. 5a, and a 18 kHz shear beam, shown in FIG. 5b, mix to form a third beam, shown in FIG. 5c, with frequency 7 kHz=25 kHz−18 kHz. In this example, in accordance with the plane wave predictions, a third back propagating P beam with frequency $(f_1-f_2)$ at an angle of 133° to the $P(f_1)$ wave is generated by nonlinear mixing in the region where the $P(f_1)$ and $SV(f_2)$ beams overlap.

The kinematics of non-linear interactions of beams results in the generation of specific combinations of wave vectors and frequencies. The third wave returns at a specific travel time, and with specific frequencies $f_3$ and wave vectors $k_3$ such as $f_3=f_1-f_2$ and $k_3=k_1-k_2$. For a combination of $f_1$, $f_2$, $k_1$ and $k_2$, there is a well-defined propagation wave vector $k_3$ of the third wave in the same plane, defined by $k_1$ and $k_2$. There is a direct correspondence between the signal detected at a particular receiver position and the location where the non-linear mixing of the two primary waves $k_1$ and $k_2$ takes place. The signal strength of the receiver would be proportional to the strength of the non-linearity of the rocks in the mixing zone, among other factors, and reach a maximum for a receiver lying on vector $k_3$. Therefore, the signal strength at the receivers can be geometrically mapped onto the non-linearity of the rocks along the beam trajectory as shown, for example, in FIG. 1.

The geometrical theory of wave propagation indicates that the beam generated in each mixing zone would arrive at the borehole at a specific receiver defined by the geometry of the three wave vectors $k_1$, $k_2$ and $k_3$, after a specific time delay. The strength of the returning signal at a specific location in the borehole at a particular time is dependent on the degree of non-linearity of the interaction location. Hence, a time image of the relative strength of the non-linear properties of the rocks along the beam can be constructed. The amplitude or magnitude of a returned signal at the receivers can be itself indicative of certain petrophysical properties of the mixing zone. If the beam and plane wave are scanned in azimuth and elevation while preserving the convergence angle, a localized circumferential and radial 3D image of non-linear properties of rocks surrounding the borehole can be obtained. By moving the entire assembly up and down the borehole, repeated 3D images of non-linear properties of rocks surrounding the borehole can be obtained. By making weighted stacks of these repeated images, a final image of non-linear properties of rocks surrounding the entire borehole can be constructed through subsequent computer processing. In addition, if the sources and the receivers are part of three separate tool bodies, one or two can be moved while the third one is fixed (for example, the sources are fixed while the receiver tool body is moved up and down). Alternatively, several descents into the well may be made with different spacing between the tool bodies.

For non-linear mixing between an elastic beam and a broader beam (quasi plane wave), the selection rule is relaxed. Third waves of frequency $f_1-f_2$, centered around the wave vector $k_3=k_1-k_2$, are generated continuously along the primary beam if the beam width is about ten wavelengths of the third wave. The resulting signal strength for $f_3=f_1-f_2$ is a function of the average non-linear properties of the mixing region, the average ratio of velocity of $f_1$ propagation and average velocity for $f_2$ propagation (noting that beams with frequencies $f_1$ and $f_2$ may be compressional or shear), the volume of the mixing zone and the geometry of the mixing. This function can be computed for various mixing modes. For example, the signal strength for a particular mixing mode such as compressional wave P for $f_1$ and SV for $f_2$ is given by $$U = 2\pi^2 \beta_{PS_vP} A_1 B_2 \frac{f_1 f_2 (f_1 - f_2)}{V_P^2 V_s} \frac{V_{PS_vP}}{L} F_{PS_vP} \Delta_{PS_vP} \quad (1)$$

where U is the displacement amplitude of the third wave received at the borehole, $A_1$ is the longitudinal polarization of the compressional wave and $B_2$ is the transverse polarization of the shear wave. β is a function of the A, B and C parameters of Landau and Lifschitz representing the non-linearity of the rocks in the mixing zone. v is the volume of the mixing zone, L is the distance from mixing zone to the receiver. F is the geometric form factor of order 1 which is dependent on the geometry of the incident beams and can be numerically computed for the particular geometry. Δ is a selection rule form factor which is a numerically computable function of the wave vectors $k_1$, $k_2$ and $k_3$ and is only significant if the interaction geometry honors the selection rules. The subscript $PS_rP$ in the formula refers to compressional-shear interaction generating a compressional wave.

Figure 6:
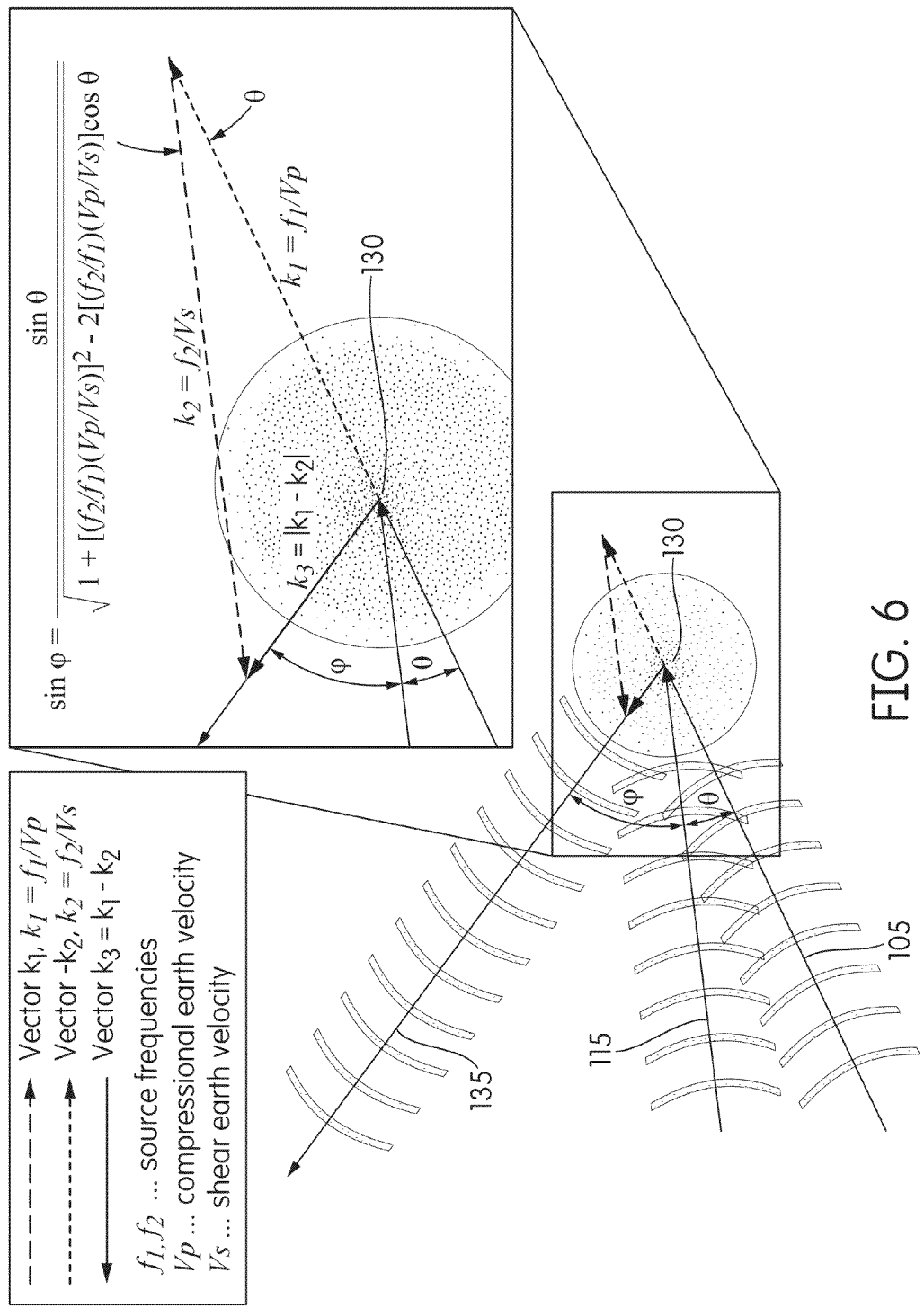
FIG. 6 illustrates the geometry of the generation of the difference frequency third wave by non-linear mixing of two primary acoustic waves as governed by the non-linear mixing selection rule.

In accordance with certain aspects of this disclosure, an image of the compressional to shear velocity ratio may be constructed as follows. When one of the sources generates a compressional wave (P-wave) with frequency $f_1$ and the other source generates an SV-wave with frequency $f_2$ and both waves are steered towards a specific intersection volume, the propagation direction of the third compressional wave (P-wave) with difference frequency $f_3=f_1-f_2$ is controlled by the average in situ Vp/Vs velocity ratio of the rock in the mixing zone as governed by the selection rules as shown in FIG. 6. From the measurements of the signal in the three component receiver array 145 on FIG. 2 or FIG. 3, the direction of this third wave can be determined and thereby, the in situ Vp/Vs of the mixing zone can be computed. If the beam and plane wave are scanned in azimuth and elevation while preserving the necessary convergence angle, a localized circumferential and radial 3D image of in situ Vp/Vs ratio of rocks surrounding the borehole can be obtained. By moving the entire assembly up and down the borehole, repeated 3D images of in situ Vp/Vs of rocks surrounding the borehole may be obtained. By making weighted stack of these repeated images, a final image of in situ Vp/Vs of rocks surrounding the entire borehole can be constructed through subsequent computer processing. Alternatively, several descents into the well may be made with different fixed spacing between the tool bodies.

In some aspects of this disclosure, an alternative determination of Vp/Vs ratio is achieved through scanning the ratio of the frequencies $f_1$ to $f_2$ of the primary beams. FIG. 6 illustrates the geometry of the interaction of two beams such as those generated in the configuration of FIG. 1, that may be analyzed using the vector mathematics and trigonometry. The lengths $k_1$ and $k_2$ of vectors $k_1$ and $k_2$ are defined by the ratio of their corresponding frequencies and velocities. As shown in FIG. 6, the returning angle φ is a function of $f_1/f_2$, Vp/Vs ratio and the intersection angle θ of the two primary beams. In addition, the physical selection rules only permit the generation of a third wave at specific combinations of $f_1/f_2$, Vp/Vs ratio and angle of interception θ, such as the example illustrated on FIG. 5.

Using the symbol r for the Vp/Vs ratio and the terms defined on FIG. 6, the magnitude $k_3$ of vector $k_3$ is given by the vector sum of $k_1$ and $-k_2$, that is $$k_3 = |k_1 - k_2| = \frac{f_1 - f_2}{V_P}$$

and also by the cosine rule that states $k_3^2 = k_1^2 + k_2^2 - 2k_1 k_2 \cos\theta$.

Combining the two equations, and substituting $f_1/Vp$ for $k_1$ and $f_2/Vs$ for $k_2$, leads to a statement of the geometric conditions imposed by the selection rules. The quadratic equation $$\frac{f_2}{f_1} r^2 - 2r\cos\theta - \frac{f_2}{f_1} + 2 = 0$$

may be solved for r, the Vp/Vs ratio of the mixing zone. This leads to a non-limiting alternative method for measuring in situ Vp/Vs ratio of a particular mixing region by the following sequence: a) record a standard sonic waveform log to determine Vp and Vs near the borehole to acquire data to estimate the phase differences between adjacent elements in a phased source array to steer the beams at the approximate convergence angle for the geometry of the planned measurement; b) steer the P and SV sources to converge at a controlled angle θ and mix at a particular region in space surrounding the borehole; c) vary $f_2$ while fixing $f_1$ and measure the amplitude of the received signal at the difference frequency $f_1-f_2$ at the sensors in the borehole; d) identify the frequency at which the signal each receiver in the array reaches a maximum amplitude strength; and e) determine angles θ and φ from the geometry of the sources and receivers. By sweeping the beams in elevation, rotating in azimuth, and moving the entire assembly up and down the borehole and repeating the above procedure, the Vp/Vs ratio of a 3D volume around the borehole is interrogated and thereby 3D images of in situ Vp/Vs ratio of rocks surrounding the borehole may be obtained.

The methods described above provide that the frequency difference $f_1-f_2$ is very specific, allowing for spectral analysis to enhance the signal to noise ratio of the measurements. Moreover, if both frequencies $f_1$ and $f_2$ are simultaneously chirped proportionally, the resulting difference frequency signal $f_1-f_2$ would also be a well defined chirped signal. The time-varying code may include one or more of a variation in amplitude, a variation in frequency, and/or a variation in phase of the first, the second, or both the first and the second beams or waves. The third difference wave can be broadband if one of the primary frequencies is swept through a range of frequencies while their frequency ratio is fixed. Thus, the resulting third beam $f_2-f_1$ will be swept across a wide frequency range, while preserving the same direction. This allows for improvement in signal to noise by standard autocorrelation of the chirped or coded signal.

Since the wave vector $k_3=k_1-k_2$ is well defined, the signal to noise discrimination of the recorded third wave from receivers 135 can be enhanced further by employing three-component receivers in the borehole. For example, the signals from the three components can be tuned to specific directivity by a technique, such as, hodogram analysis.

In some aspects of the present disclosure, the signal to noise ratio can be improved by repeating the above steps and using an inverse polarity (180 degrees out of phase) source signals and adding the results together. The returning difference frequency signal will add coherently as its amplitude is proportional to the product of the amplitudes of the two primary waves and therefore will not reverse polarity when the polarity of the primary source is reversed. On the other hand, any linear noise generated by the primary sources in the system will reverse polarity and thus cancel upon addition.

Alternative methods can be devised with various non-exclusive combinations of beams and waves. By way of a non-limiting example, a method to generate images by computer processing of acoustic and seismic signals includes the following steps. First, the method performs spectral analysis of the frequency content of the recorded third wave and applicable selection rules of the difference frequency signal in order to isolate the third wave signal generated by the non-linear mixing process. In the case that the sensors include three component geophones, determine the direction of the third wave impinging on the borehole using orientation techniques. The method continues by analyzing the amplitude of the recorded third wave as a function of frequency ratios of the primary mixing waves and determining the mixing location where the third wave signals originated, from the selection rules of non-collinear mixing in non-linear media, the wavenumbers of the first and second beams and the third wave and the locations of the two beam sources and the sensor array. The method continues by constructing seismograms determined by cross-correlation of the received signals with chirped transmitter signals for each source-receiver combination. The method continues by performing three dimensional time or depth imaging to the entire data set, in order to obtain three dimensional images of the non-linear properties of the formation surrounding a borehole in either or both of time and distance. The methods for generating images from seismograms are known, for example, Hill et al., which is hereby incorporated by reference, have provided the general methodology for the special case of imaging from beams.

Figure 7:
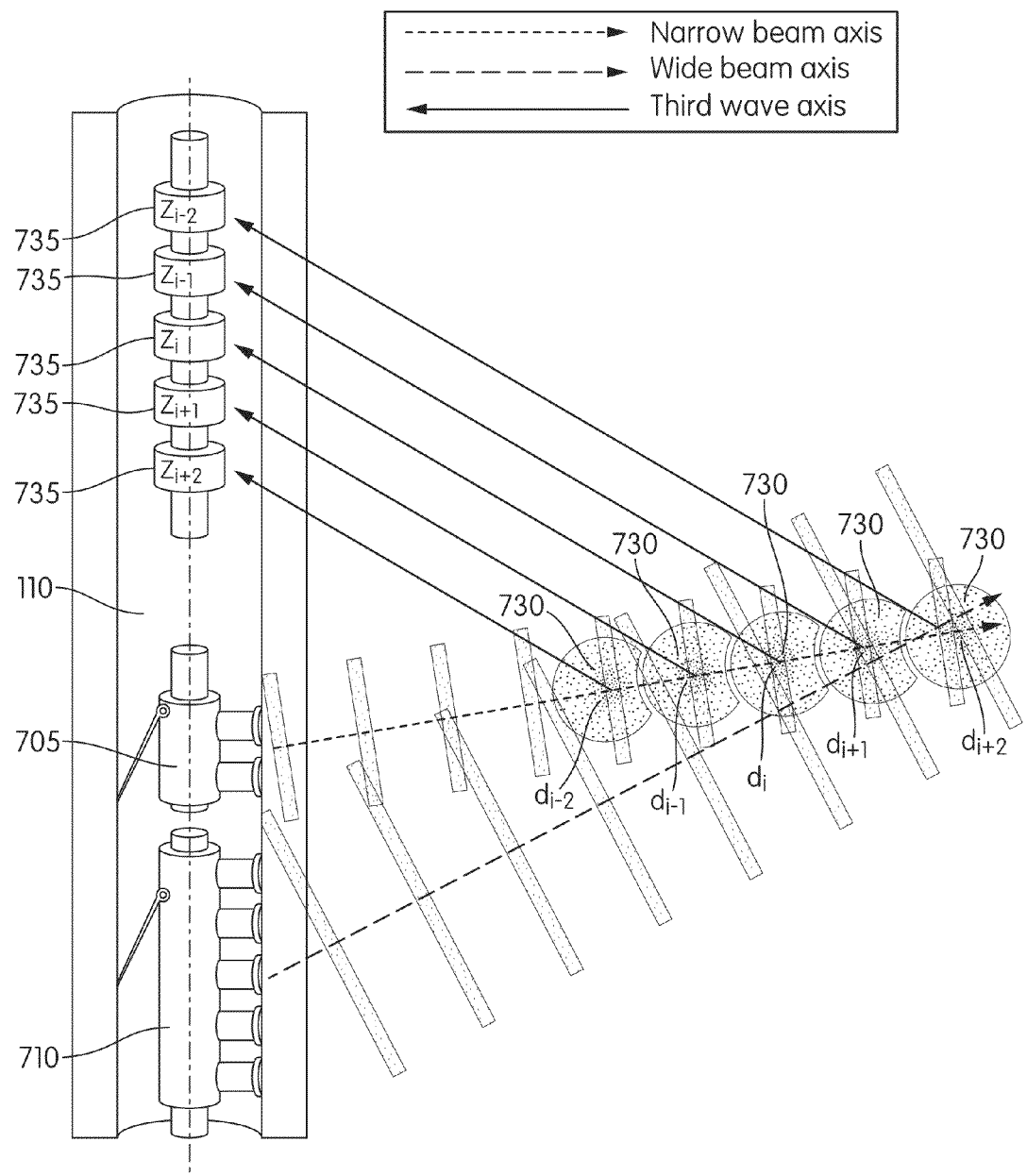
FIG. 7 shows an application of aspects of the present disclosure for imaging using a beam and broad beam or plane wave.

Another non-limiting alternative imaging method is illustrated in FIG. 7, which shows the case of interactions of a narrow 705 and a broad (wide) beam 710. Given a smooth background model of Vp and Vs of the investigated volume, application of the selection rules enables the geometric mapping of the energy detected at a receiver location 735 on to mixing zones 730 along the narrow beam. A time image of the non-linear property can thus be constructed along the narrow beam. By rotating in azimuth and moving the assembly along the borehole, a three dimensional time image can be constructed of a volume centered on the borehole. Successive repetition of the measurement at different beam elevations, and altering the $f_2/f_1$ frequency ratio yields a series of three dimensional time images. This redundancy in imaging permits further refinement of the smooth background model and a three dimensional spatial image.

Non-linear parameters of rocks have been found to be related to a number of important hydrocarbon reservoir parameters, such as variations with gas, oil and water saturation, effective stress, fracture density and mineralogical content. In certain aspects of this disclosure, the 3D images of non-linear properties constructed by the above method are transformed to provide quantitative information on the distribution of these properties around the borehole at the time of recording. In addition, sequential repetitions of this method are used to detect changes in reservoir properties over time for reservoir monitoring purposes.

The recordings of received waveforms are processed to generate an image of the non-linear characteristics of the formation. The directivity of the beam and the time of flight may fix the locations where scattered waves are generated, thus, distinguishing this method from normal sonic imaging techniques using conventional non-directional monopole and dipole sources.

By way of a non-limiting example, when a primary compressional (P) wave with a frequency $f_1$ and a primary compressional (P) wave with a frequency $f_2$ cross in a non-linear medium, and the selection rules are honored, a third shear (SV) wave can be generated with a frequency $f_1-f_2$. This particular configuration can be used for creating 3D images of the Vp/Vs velocity ratio and non-linear properties of the rock formations around the borehole for many ranges of distance of investigation from a borehole. This particular example of compressional non-linear mixing to generate a shear wave (i.e., P+P➔ SV) will be used to describe a number of new concepts, methodologies, processes and systems for measurement and analysis purposes in the following paragraphs. These are equally applicable to P+SV➔ SV or any permutation of non-linear mixing of two acoustic compressional or shear waves to generate a third wave.

Figure 8:
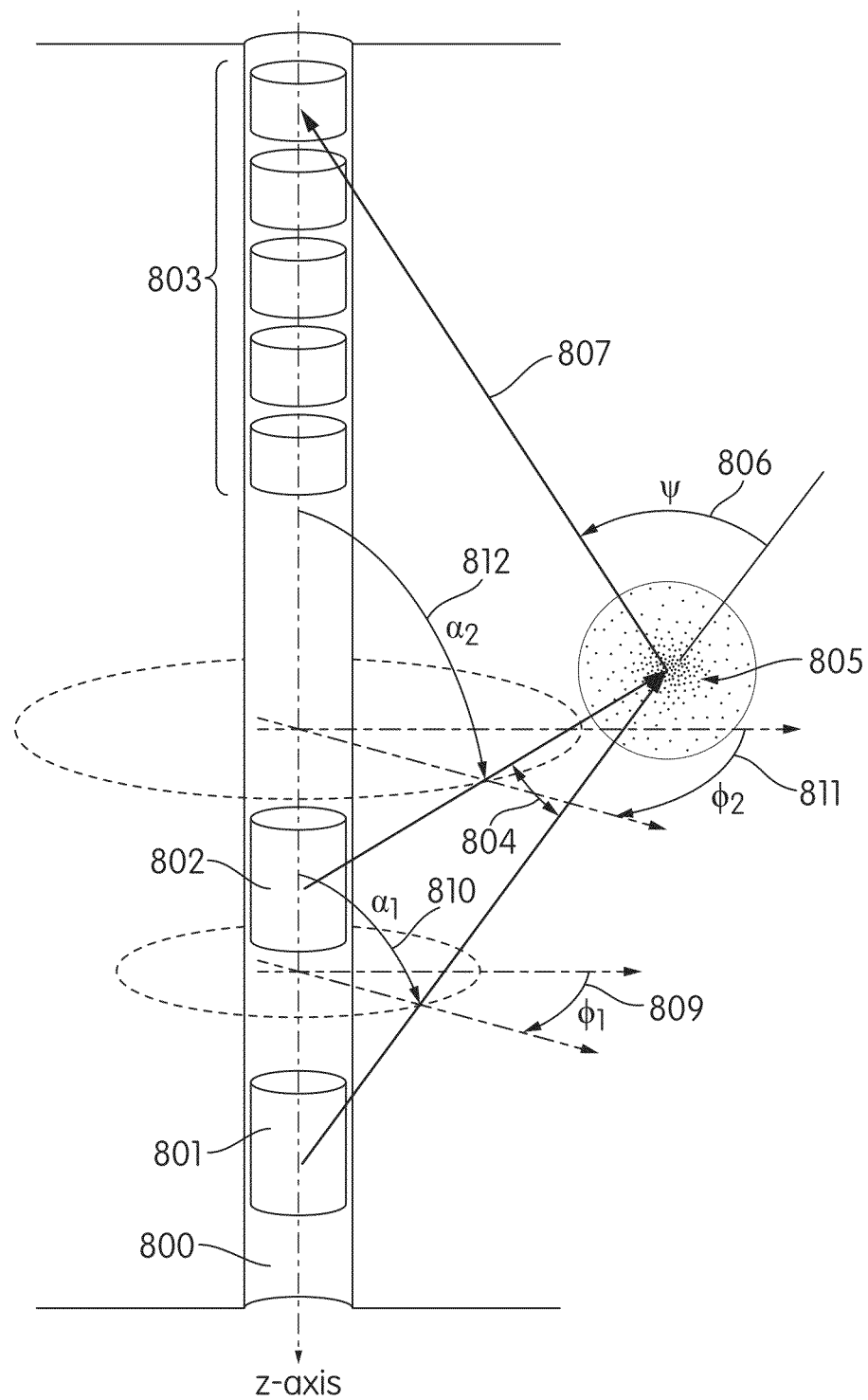
FIG. 8 shows an example configuration for a borehole-based system for remote mapping of non-linear properties and/or Vp/Vs ratio of rock formations using non-collinear acoustic mixing, in accordance with an aspect of the present disclosure.

FIG. 8 shows an example configuration for a borehole-based system for remote mapping of non-linear properties and Vp/Vs velocity ratio of rock formations using non-collinear acoustic mixing in accordance with an aspect of the present disclosure. Two primary acoustic beams, for example compressional (P) waves, from upper and lower arrays of transmitters 801 and 802 located in borehole 800, are directed into the rock formation surrounding the borehole. The transmitter arrays can be oriented such that acoustic energy propagates at any azimuth $\phi_1$ 809 and $\phi_2$ 811 and elevation $\alpha_1$ 810 and $\alpha_2$ 812 relative to the borehole axis. For suitable elevation angles $\alpha_1$, $\alpha_2$, and azimuth angles $\phi_1$ and $\phi_2$, the two primary P beams propagating through the rock formation intersect with convergence angle $\theta$ 804 at an mixing zone 805, remote from borehole 800. The convergence angle $\theta$ is defined as the angle between the directions of the two converging beams, represented on FIG. 8 as the lines joining the two transmitters 801 and 802 to the mixing zone 805. If the rock formation at the point of intersection has non-linear properties, a secondary (S) shear wave SV (e.g., a shear wave polarized in the plane defined by the axes of the two intersecting compressional waves) is generated due to non-linear interaction. The secondary shear wave propagates in a direction defined by the selection rules, represented by scattering angle, $\psi$, 806. The scattering angle $\psi$, is defined as the angle between the axis of the acoustic wave from the lower transmitter and the axis of the scattered wave. In the configuration shown, energy 807 returns to the borehole and is recorded at receiver or array of receivers 803.

As discussed above, the conditions suitable for generation of a secondary shear wave can be inferred from the selection rules that can be derived by the conservation of energy and conservation of momentum. The secondary wave S must obey either of the following conditions $$f_3 = f_1 - f_2 \quad (2)$$

$$k_3 = k_1 - k_2 \quad (3)$$

or $$f_3 = f_1 - f_2 \quad (4)$$

$$k_3 = k_1 + k_2 \quad (5)$$

where $k_1$, $k_2$ and $k_3$ are wave vectors. The first frequency condition, where $f_3 = f_1 - f_2$, is of particular interest for investigating properties of rock formation near a borehole. As shown in FIG. 9, the conditions (2) and (3) can be represented by the formation of the wave-vector triangles and satisfied by the following relationships (6), (7) and (8).

$$|k_3| = 2\pi |f_1 - f_2|/Vs = (|f_1 - f_2|/Vp) \times (Vp/Vs) \quad (6)$$

$$|k_1| = 2\pi f_1/Vp \quad (7)$$

$$|k_2| = 2\pi f_2/Vp \quad (8)$$

Figure 9A:
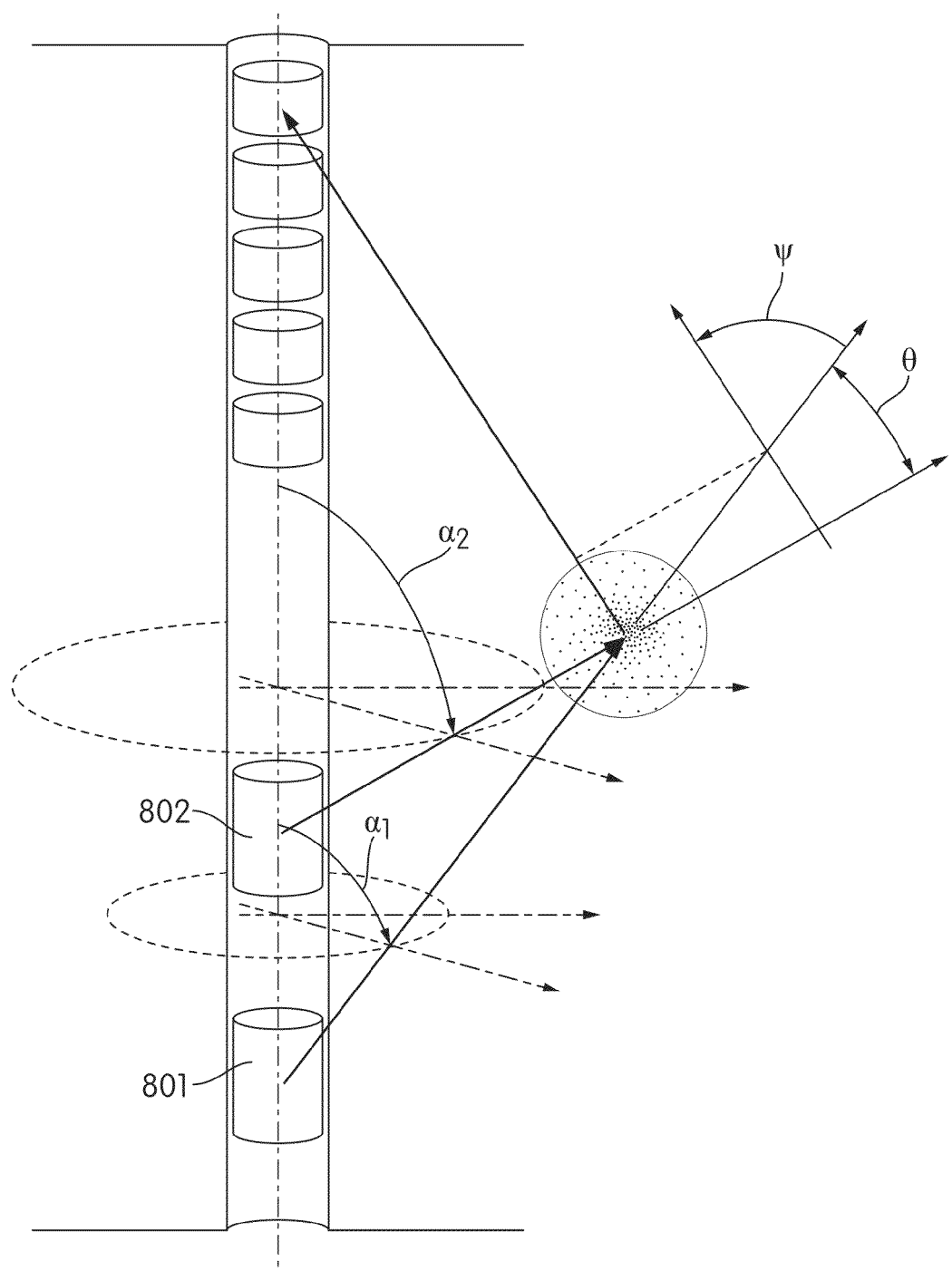
FIG. 9a shows the configuration of FIG. 8 for the purposes of identifying vectors representing the broadcast and scattered acoustic waves.
Figure 9B:
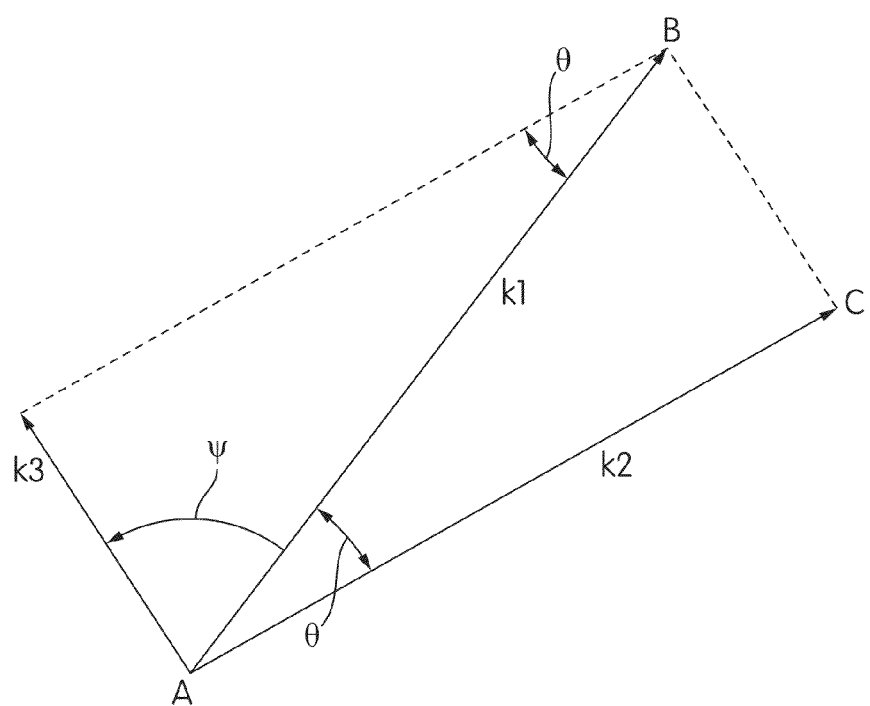

Using trigonometry in the vector diagram of FIG. 9b, it can be shown that these conditions can be met when equations (9) and (10) as satisfied.

$$\sin(\theta/2) = \left(1 - \frac{f_2}{f_1}\right) \frac{\sqrt{(Vp/Vs)^2 - 1}}{2\sqrt{\frac{f_2}{f_1}}} \quad (9)$$

$$\sin(\psi) = (f_2/f_1) \times \sin(\theta)/(1 - f_2/f_1) \quad (10)$$

Since the Vp/Vs velocity ratio is in the range 1.5 to 3.0 for many sedimentary rocks, there are combinations of convergence angle θ and frequency ratio f1/f2 (denoted herein as d) that permit the generation of a secondary shear wave SV that propagates back to the borehole in the configuration shown in FIG. 9a.

As discussed above, the behavior of acoustic energy generated by non-linear interaction of intersecting non-collinear planar waves can be calculated. The selection rules define a set of permitted interactions. The P+P→SV interaction is additional to the partial listing on Table 1. These various interactions use certain combinations of convergence angle, frequency ratio and scattering angle that depend on whether the converging waves are compressional or shear, on the Vp/Vs velocity ratio of the material at the interaction location, and differ for interactions generating sum ($f_1+f_2$) and difference ($f_1-f_2$) frequency energy. The geometry presented in the following examples is based on the P($f_1$)+P($f_2$)⇒SV($f_1-f_2$) interaction, and analogs could equally be presented for other permitted interactions generating difference or sum frequency resonance, for example, but not limited to, interactions including P($f_1$)+SV($f_2$)⇒SV($f_1-f_2$) and P($f_1$+SV($f_2$)⇒P($f_1-f_2$).

Figures 10A, 10B, 10C:
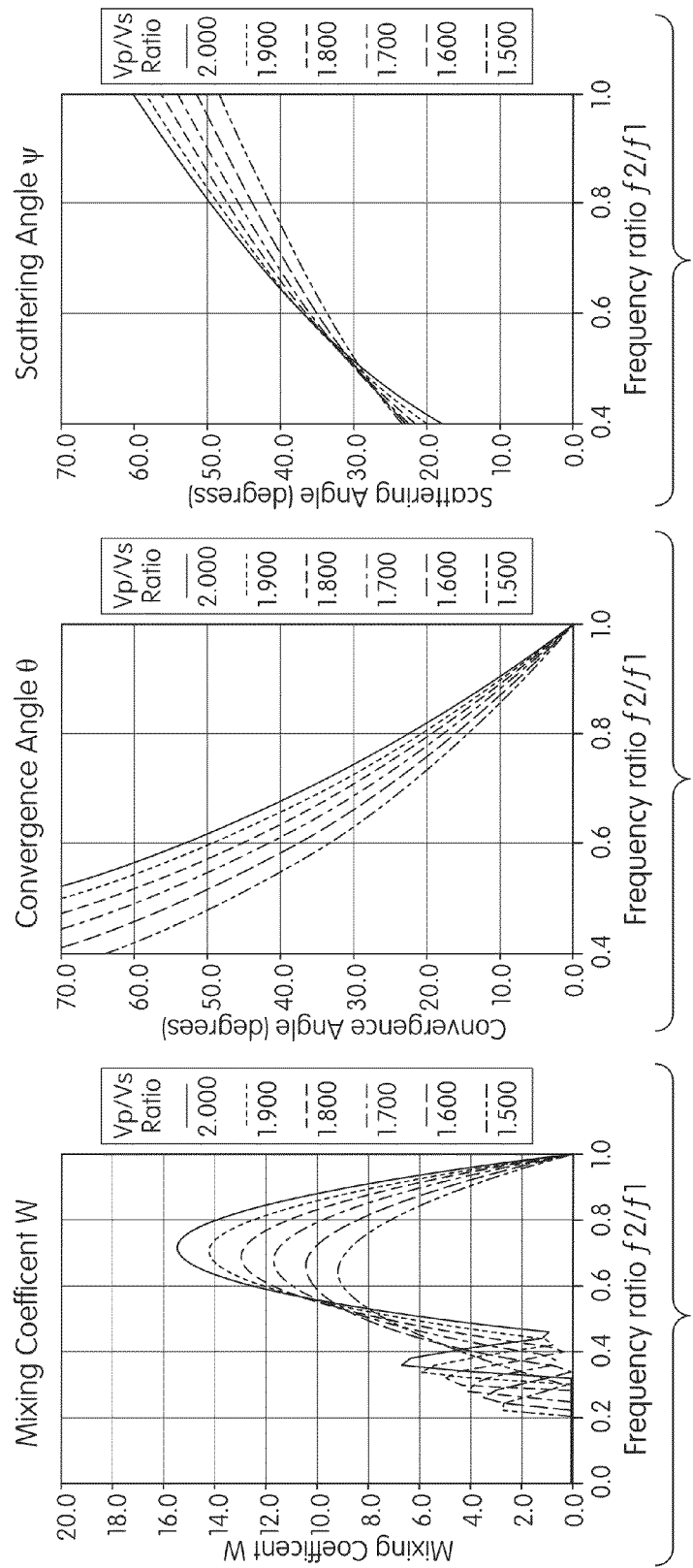
FIG. 10a shows a representative dependence of mixing coefficient on the plane wave frequency ratio for a range of mixing zone compressional velocity and shear velocity ratios Vp/Vs, in accordance with aspects of the present disclosure.
FIG. 10b shows a representative dependence of convergence angles with plane wave frequency ratio that honor the selection rules for the P+P⇒SV interaction.
FIG. 10c shows a representative dependence of scattering angles with plane wave frequency ratio that honor the selection rules for the P+P⇒SV interaction.

For example, considering P($f_1$)+P($f_2$)⇒SV($f_1-f_2$), FIG. 10a shows mixing coefficient W as a function of the frequency ratio of the two sources. The mixing coefficient W, which is a measure of the amplitude of the efficiency of the conversion generating the scattered wave, is given by equation (11).

$$W = D \frac{(1 + f_1/f_2)}{2(Vs/Vp)} \sin(2\theta) \times m \quad (11)$$

where D depends on the Lamé coefficients λ and μ and is proportional to $f_2/f_1$ for a given mixing zone, as defined in equation (12).

$$D = \frac{f_1/f_2}{4\pi(\lambda + 2\mu)} \quad (12)$$

θ is the convergence angle of the two primary beams at the mixing zone, and m is a scaling factor related to the Landau-Lifshitz non-linear constants A and B, as expressed in equation (13), $$m = \frac{A}{2} + B \quad (13)$$

Hence, m is constant for a given mixing zone.

FIGS. 10a, 10b and 10c show the dependence of mixing coefficient W, convergence angle and scattering angle on Vp/Vs velocity ratio in the range from 1.5 to 2.0 at the mixing location, assuming a representative value (from Korneev, Nihei and Myer 1998) for m of −3660 GPa. FIG. 10a shows the dependence of mixing coefficient on the plane wave frequency ratio for a range of mixing zone Vp/Vs ratios. FIGS. 10b and 10c show the corresponding convergence and scattering angles that honor the selection rules for the P+P⇒SV interaction. As can be understood from FIG. 10a, the mixing coefficient reaches a maximum at a ratio of the second frequency f2 to the first frequency f1 equal to about 0.7. In addition, from FIG. 10b, it can be appreciated that when the ratio of the second frequency f2 to the first frequency f1 is equal to about 0.7, the convergence angle is in the range between about 30 deg. and about 40 deg. Moreover, it can also be appreciated that when the ratio of the second frequency f2 to the first frequency f1 is equal to about 0.7, a scattering angle of the returning wave relative to a direction the first wave is equal to about 40 deg.

Figure 11A:
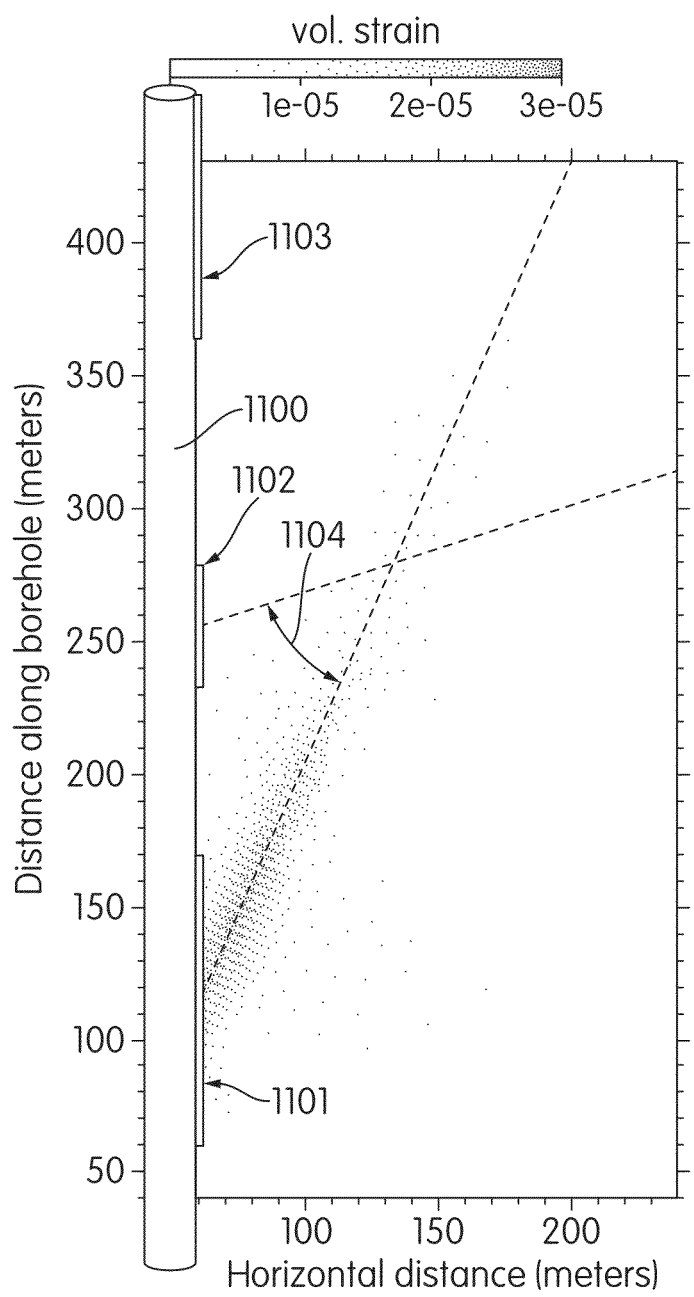
FIGS. 11a to 11c show example results of a numerical simulation of non-collinear interaction of plane waves in a non-linear medium leading to the generation of a scattered wave that returns to the borehole, in accordance with aspects of the present disclosure.
Figure 11B:
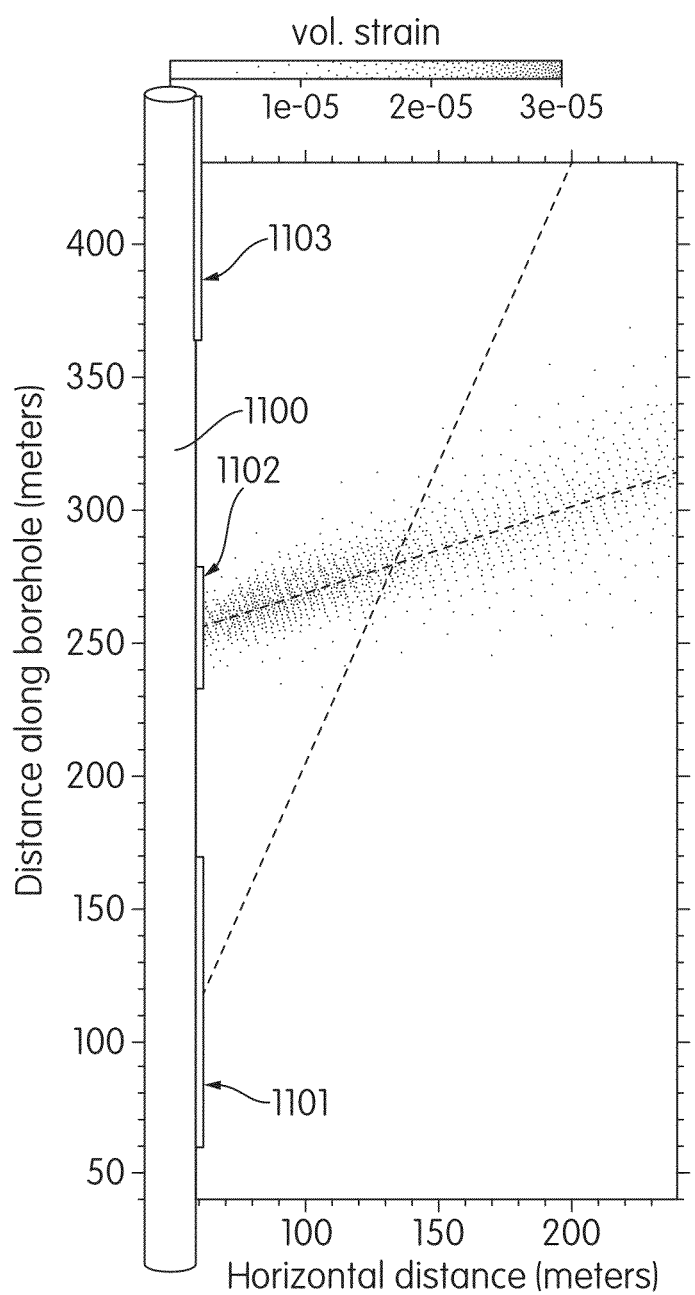
Figure 11C:
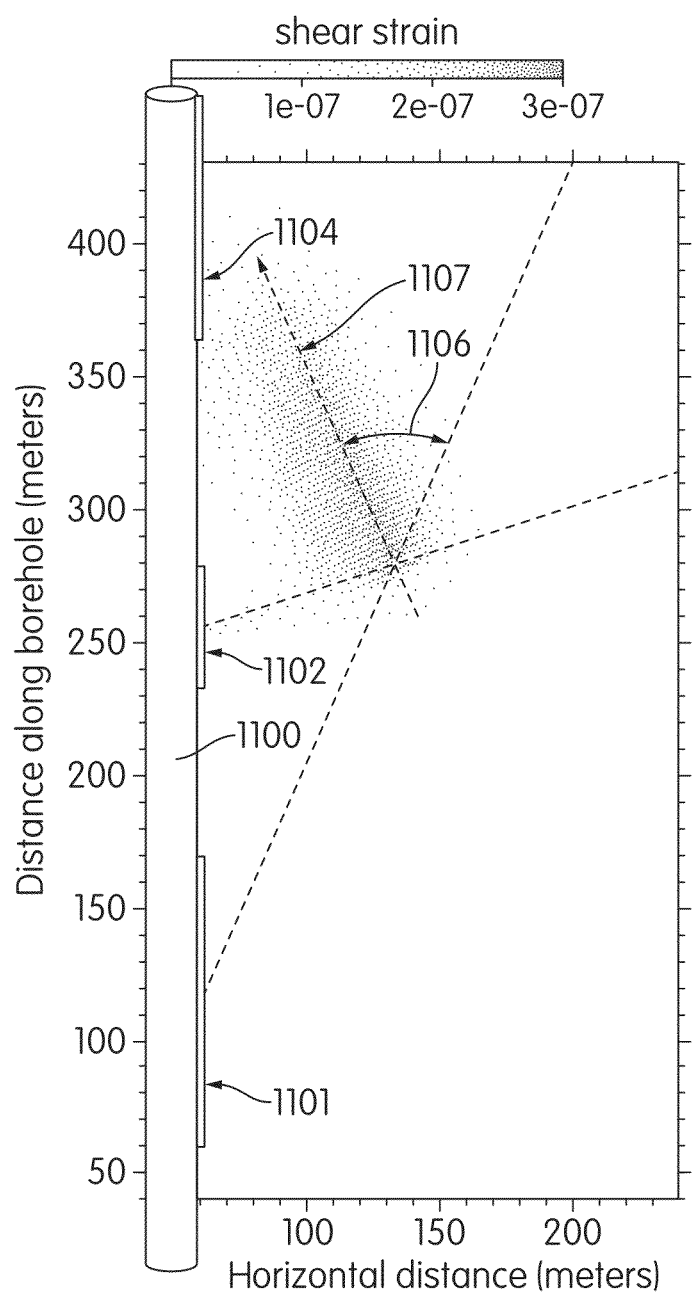

FIGS. 11a to 11c show example results of numerical simulations of non-collinear interaction of acoustic beams in a non-linear medium leading to the generation of a scattered wave that returns to the borehole. In FIGS. 11a to 11c, borehole 1100 includes lower transmitter 1101, upper transmitter 1102 and receiver array 1103. Acoustic energy in the form of a compressional beam generated by lower transmitter 1101 and upper transmitter 1102 converges at a distance from borehole at convergence angle 1104. Receiver array 1103 is arranged to receive scattered wave 1107 which is produced by the interaction of the acoustic beams as defined by the selection rules, described above and again below, at scattering angle 1106. In FIGS. 11a, 11b and 11c, distance along the borehole in meters is shown versus radial distance away from borehole in meters. In FIGS. 11a and b, the volumetric strains associated with the compressional acoustic energy of the two beams produced by the two sources are shown. In FIG. 11c, the shear strain associated with the scattered shear wave 1107 is shown.

Figure 12A:
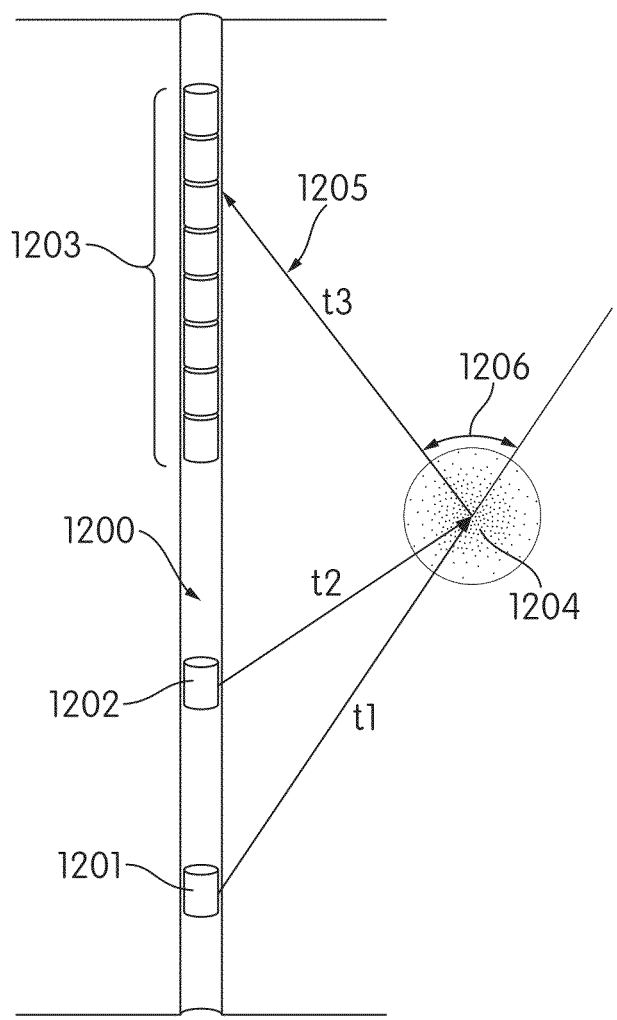
FIG. 12a shows an example representation of the directions and the times of flight for the primary and scattered acoustic waves in accordance with aspects of the present disclosure.
Figure 12B:
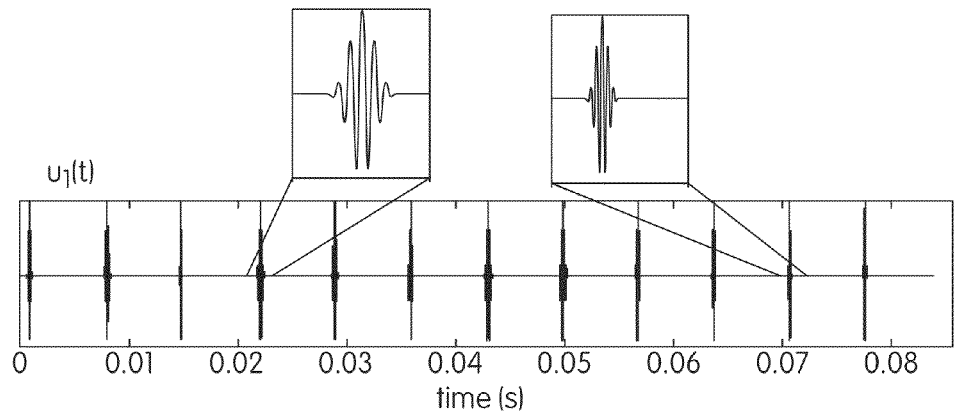
FIGS. 12b-12d show an example of a simulated signal from a first acoustic source, a simulated signal from second acoustic source, and a simulated template signal, according to an embodiment of the present disclosure.
Figure 12C:
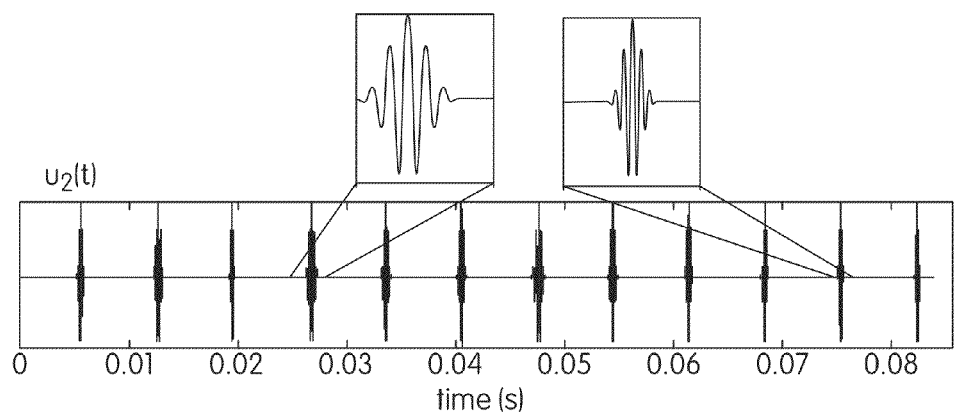

In the following paragraphs a coded scheme that can be used to enhance or extract measured scattered acoustic waves that originate from non-linear mixing of primary acoustic signals in a mixing zone within a rock formation around the borehole is described. Measurements of scattered acoustic waves generated from non-linear acoustic phenomena in rock formations away from the borehole can be enhanced by broadcasting coded primary acoustic signals, recording the returning signal from the non-linear interaction and subsequently using a waveform recognition method and/or a band pass filtering method based on the forecast properties of the non-linear signal. One non-limiting example is to correlate the recorded signal with a template representing a forecast of its timing and frequency content derived from the broadcast parameters in accordance with the selection rules. The result of this correlation represents an acoustic pulse traveling past the borehole. For example, in the case of the P+P➔ SV interaction, the returning energy resulting from the non-linear interaction appears to travel along the borehole at a velocity equal to the shear wave velocity of the formation divided by the cosine of the angle between its propagation direction and the borehole axis. When applied to a system such as that illustrated in FIG. 8, the coding and correlation method improves the detection of the weak non-linear signal and thereby enhances the construction of 3D images of non-linear properties and Vp/Vs velocity ratio in the volume probed by the measurement One non-limiting implementation for utilizing coding and signal correlation for the enhancement of signals generated by non-collinear acoustic mixing in a non-linear medium is described in the following paragraphs. A detailed description of a more general implementation of the coding scheme can be found in U.S. patent application Ser. No. 13/292,948 entitled "System and Method for Generating Micro-Seismic Events and Characterizing Properties of a Medium With Non-Linear Acoustic Interactions," filed concurrently with the present application, the entire contents of which is incorporated herein by reference. Referring to FIGS. 12a through 12d, source 1201 starts to broadcast a first coded or modulated time train $u_1(t)$, consisting of a sequence of N acoustic pulses, at time t=0. The nth acoustic pulse has frequency $f_n$ and an amplitude envelope $E1_n(t-T_n)$ of limited time duration, where n=1, 2 ... N and $T_n$ is the broadcast time of the nth pulse. The time separation between sequential pulses is variable. In some embodiments, the time separation between sequential pulses is much longer than the time duration of the individual pulses and the pulses do not overlap. A second coded or modulated time train, $u_2(t)$, is broadcast from source 1202. This second coded or modulated time train consists of a sequence of N sequential acoustic pulses and starts at time t=δ, where δ is a start time difference between a start time of a broadcast of the first coded train and a start time of a broadcast of the second coded train. In one embodiment, the start time difference can be understood as a time delay between the broadcast of the first coded train and the second coded train. As it can be appreciated, the broadcast of the first coded train can be delayed relative to the broadcast of the second coded train or vice versa. In the present description it is often referred to δ as being a "time delay". However, δ should be interpreted broadly to be a "time difference" as the second pulse sequence may start before the first. The nth acoustic pulse has frequency $d \cdot f_n$ and an amplitude envelope $E2_n(t-(T_n+\delta))$ of limited time duration, where n=1, 2 ... N. The frequency ratio between corresponding pulses in the two trains is fixed at d. $T_n+\delta$ is the broadcast time of the nth pulse. The amplitude envelopes E1 and E2 of the first and second coded signal trains, respectively, can be different or the same. Examples of the time coded signal trains are shown in FIGS. 12b-12c. These coded signals can be represented mathematically by following formulas (14) and (15). In the present description the symbol "·" is used for as a multiplication operator.

$$u_1(t) = \sum_n E1_n(t - T_n) * \exp(i2\pi * f_n * (t - T_n)) * \exp(i\zeta_n) \quad (14)$$

$$u_2(t - \delta) = \sum_n E2_n(t - (T_n + \delta)) * \exp(i2\pi * d * f_n * (t - (T_n + \delta))) * \exp(i\zeta_n) \quad (15)$$

where $\zeta_n$ is a phase of each pulse n and $\exp(i\zeta_n)$ is a phase term of each pulse n.

The respective signal envelopes $E1_n(t-Tn)$ and $E2_n(t-(Tn+d))$ can have any shape or form such as a Gaussian form, etc. Similarly, although the modulated signals within the envelopes are expressed in equations (14) and (15), they can be modeled by other mathematical formulas. When the time delay δ is equal to the difference in travel times t1 and t2 (that is to say δ=t1−t2) from transmitters 1201 and 1202 to the mixing zone 1204, the acoustic energy of corresponding pulses n from the two broadcast trains arrives simultaneously at the mixing zone and, if the convergence angle, frequency ratio and Vp/Vs ratio at the mixing location are accord with the selection rules' criteria, generates a third series of scattered acoustic pulses with dominant frequency $(1-d) \cdot f_n$, equal to the difference between the frequencies in the two primary pulses, $f_n$ and $d \cdot f_n$. This third wave, denoted $u_3$, recorded at the receiver, inherits the coding of the two primary signals and therefore may be expressed as equation (16).

$$u_3(\tau) \propto \sum_n E3_n (t - (T_n + T)) \cdot \exp(i2\pi * (1 - d) * f_n * (t - (T_n + T))) * \exp(i\zeta_n) \quad (16)$$

where $\zeta_n$ is a phase of each pulse n and $\exp(i\zeta_n)$ is a phase term of each pulse n of the third wave.

$E3_n(t)$ is the resulting amplitude envelope due the mixing of the primary pulses and T is the total travel time from the source 1 to the recording receiver via the center of the mixing zone as further explained below.

In one embodiment, signal enhancement can be accomplished using a correlation technique well known in seismic processing industry to extract a relevant part of the non-linear interaction and travel time information in measured signal $u_3$. The technique involves the construction of a template signal $u_s$ that has the coded signal form as expressed in equation (17).

$$u_s(t) = \sum_n W_n(t - T_n) * \exp(i2\pi * g(f_n) * (t - T_n)) * \exp(i\zeta_n) \quad (17)$$

where $\zeta_n$ is a phase of each pulse n and $\exp(i\zeta_n)$ is a phase term of each pulse n of the template signal.

Figure 12D:
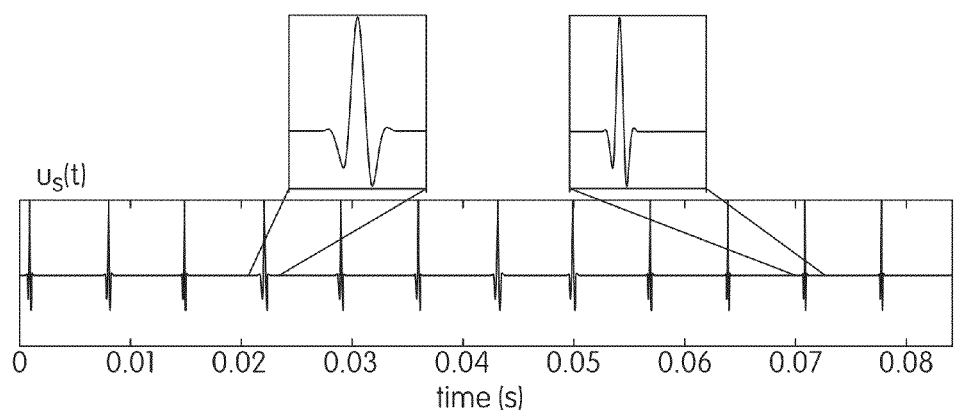
Figure 13A:
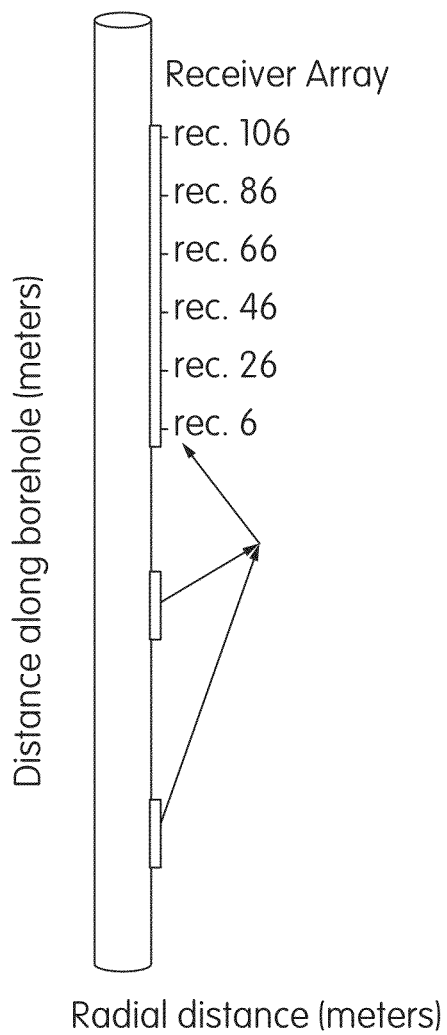
FIG. 13a shows a position of a first acoustic source and a second acoustic source and a receiver array, according to an embodiment of the present disclosure.
Figure 13B:
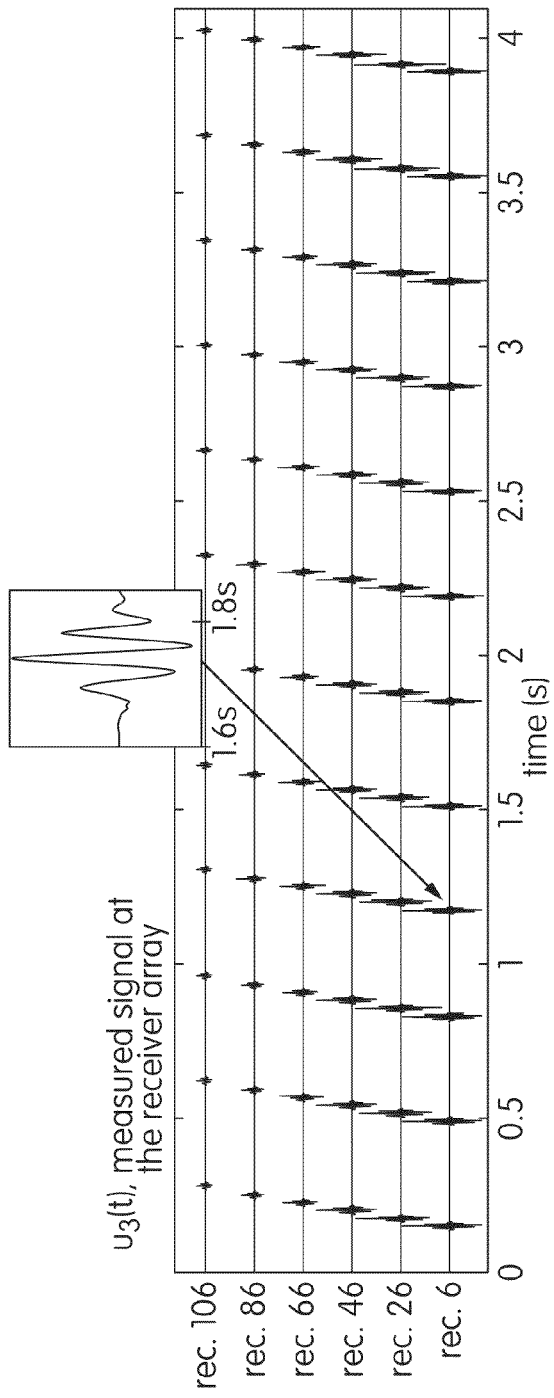
FIGS. 13b to 13d show how correlation of the received series of pulses with a modeled template signal results in identification of the signal's arrival time at the receiver array, in accordance with an embodiment of the present disclosure.
Figure 13C:
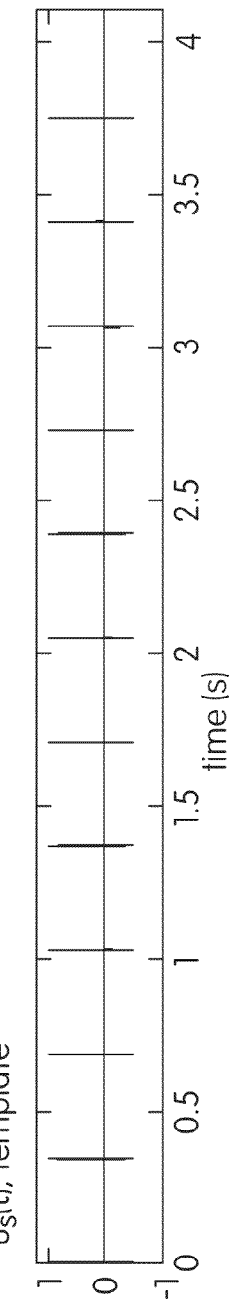
Figure 13D:
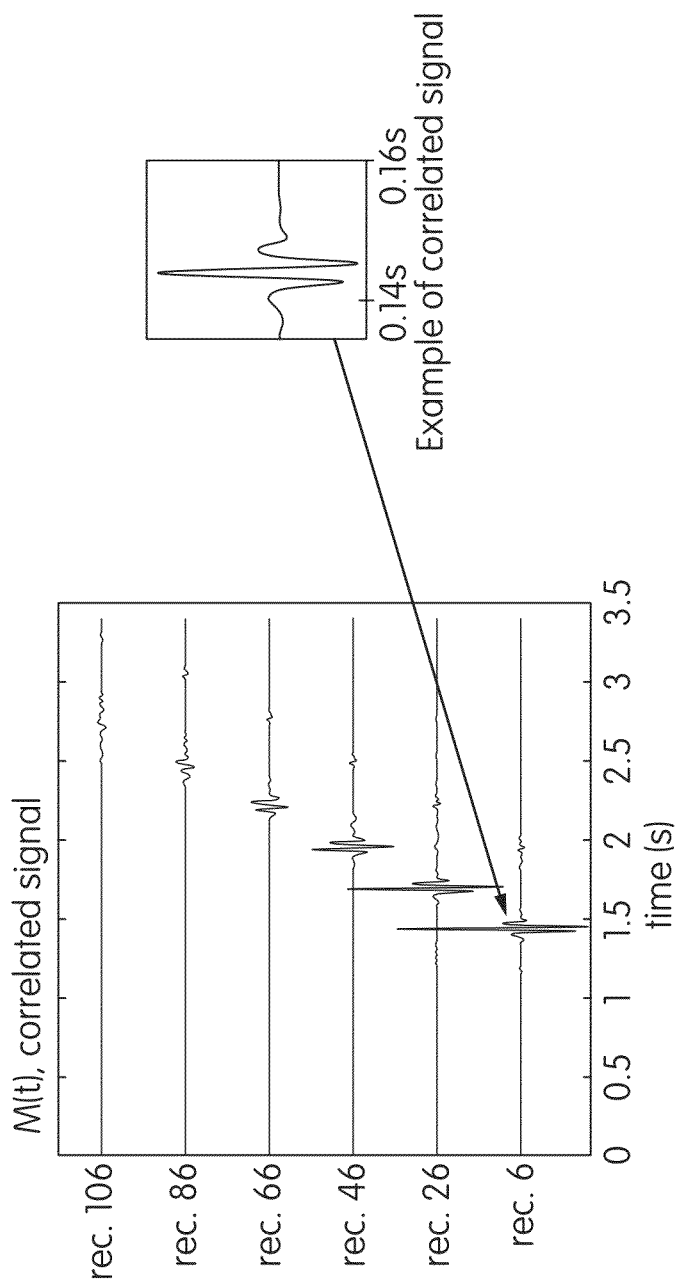
Figure 14A:
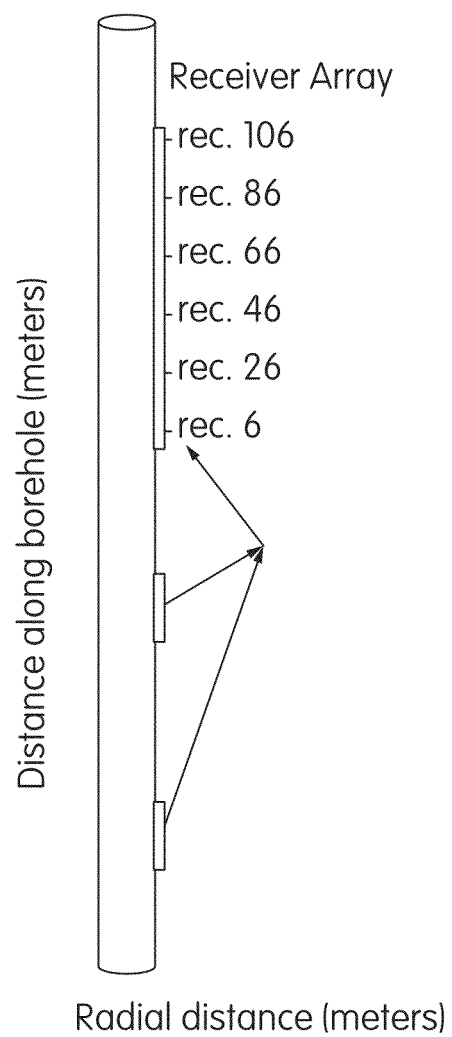
FIG. 14a shows a position of a first acoustic source and a second acoustic source and a receiver array, according to an embodiment of the present disclosure.
Figure 14B:
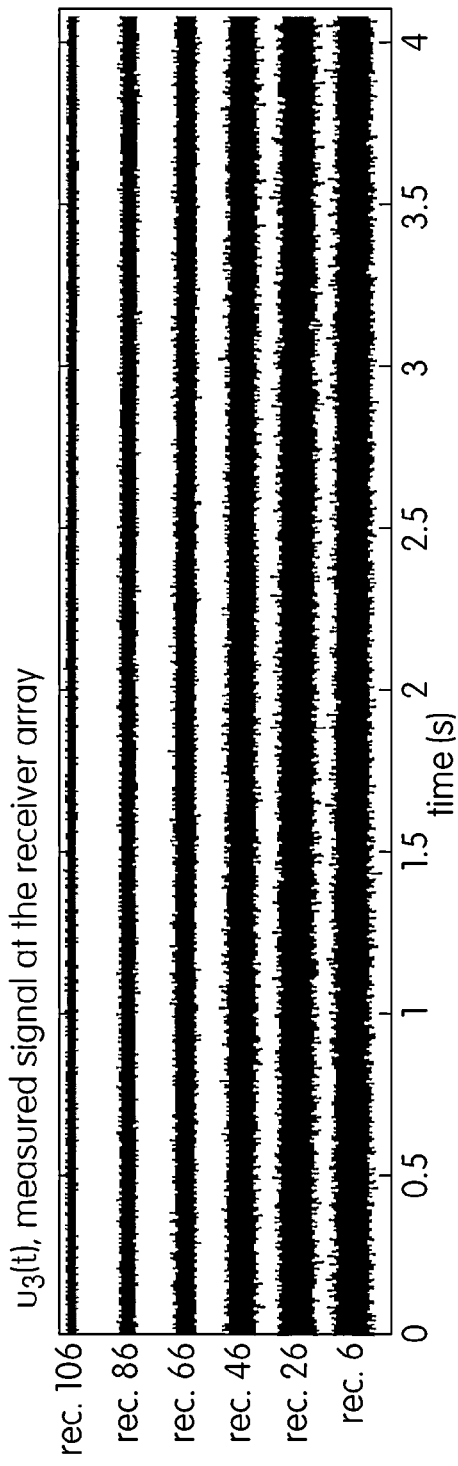
FIGS. 14b to 14d show the effect of transmitting a series of coded pulses and using correlation techniques to improve signal to noise ratio, in accordance with aspects of the invention.
Figure 14C:
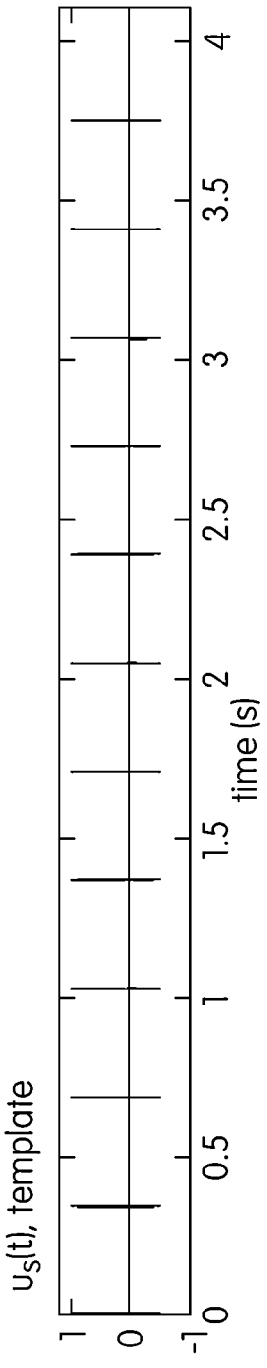
Figure 14D:
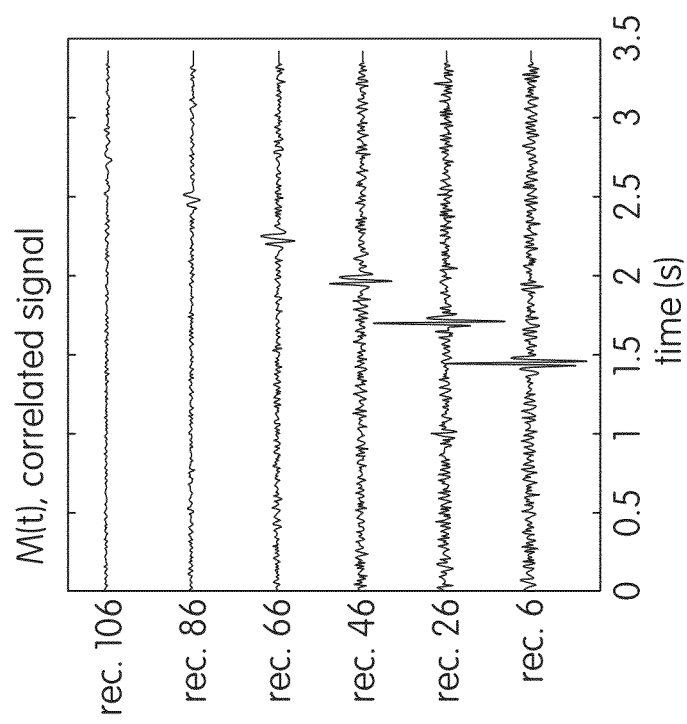

$W_n$ is some suitably chosen envelope function and $g(f_n)$ is some suitably chosen function of frequency $f_n$. The selection of an appropriate function $g(f_n)$ may be based on the shape of the expected modulated signal within the measured signal $u_3$ to achieve the best non-linear signal extraction. For example, $g(f_n)$ can be selected to be $(1-d)*f_n$ such that $u_s$ is equal to $$u_s(t) = \sum_n W_n(t - T_n) \exp(i2\pi(1 - d)(t - T_n)) \exp(i\zeta_n)$$

as shown in FIG. 12d. However, other functions $g(f_n)$ are also within the scope of the present invention.

To extract the signals from non-linear interactions in $u_3$, a cross-correlation between $u_3$ and $u_s$ can be performed to obtain the correlated signal M where M is mathematically defined by equation (18).

$$M(t) = \int u_3(t') * u_s(t-t') dt' \quad (18)$$

It can be shown mathematically that the resulting correlated signal M is a sharp band-limited spike with a bandwidth including all the frequencies $(1-d)\cdot fn$ for $n=1, 2, \ldots, N$ when the number of pulses N is large. The term "band-limited" spike is used herein to refer to a spike signal having a limited frequency bandwidth. In one embodiment, increasing the broadcast duration by increasing the number of pulses N enhances signals generated by non-linear interaction in the correlated signal M while more effectively suppressing signals generated by linear interactions and other noise. It should be noted that the correlation technique using the coded signal pattern is one of many ways to extract and enhance signals generated by non-linear interactions. Alternative signal processing techniques including pattern recognition or frequency band filtering could equally be used for signal extraction and enhancement.

The correlated measured signal M has the following properties. First, the correlated signal contains a sharp band-limited spike, corresponding to the non-linear interaction at the mixing zone, only if the time delay $\delta$ between first and second primary coded signals is equal to the difference between the travel time $t_1$ from the first acoustic source 1201 to the mixing zone 1204 and the travel time $t_2$ from the second acoustic source 1202 to mixing zone 1204, i.e. $\delta = t_1 - t_2$. If this condition is not met, the correlated signal is highly suppressed. Second, if the condition $\delta = t_1 - t_2$ is met, the band-limited spike occurs on the correlated signal M(t) at the time T which is equal to a sum of the travel time from the first primary acoustic source to the mixing zone and the travel time from the mixing zone 1204 to the receiver within the receiver array 1203, i.e. $T = t_1 + t_3 = \delta + t_2 + t_3$. Third, increasing the duration of the coded signal train, i.e., increasing the number of pulses N in the broadcast train, improves discrimination of signal from noise$_e$, because the noise does not have the form of the template signal $u_s$.

Numerical simulation results of a case where the lower transmitter 1201 and upper transmitter 1202 emit two coded signal trains consisting of sequential acoustic pulses with Gaussian envelopes are shown in FIG. 13a-13d. In this non-limiting example, coded signals of 12 pulses are used with frequency pairs (574 Hz, 373 Hz) (624 Hz, 405.6 Hz) (700 Hz, 455 Hz) (757 Hz, 492 Hz) (802 Hz, 521.3 Hz) (870.5 Hz, 566 Hz) (947 Hz, 615.5 Hz) (1000 Hz, 650 Hz) (1120 Hz, 728 Hz) (1218 Hz, 792 Hz) (1324 Hz, 861 Hz) (1440 Hz, 936 Hz). The frequency ratio $f_2/f_1$ between the pairs is a constant 0.65. The start time delay $\delta$ between the two signal trains is chosen to be equal to (t1−t2). Numerical simulation of the non-linear interaction due to the broadcast of the two coded wave trains $u_1$ and $u_2$ is performed on a computer. The simulated signals due to non-linear interaction from a broadcast of two sequential pulses received and recorded at six of 110 receivers, indexed from 1 to 110, in the non-limiting example of a receiver array 1203 are shown in FIG. 13(*b*). The template $u_s$ for the returning coded signal is shown in FIG. 13(*c*). The result of correlation between the template signal with the recorded signal at each receiver is shown in FIG. 13(*d*). The resulting correlated signal at each receiver shown in FIG. 13(*d*) shows a very sharp band-limited spike. This sharp spike occurs at the time T=t1+t3 where t1 is the travel time from the source 1 to the center of the mixing zone and t3 is the travel time from the center of the mixing zone to the receiver. The time delays or "move-out" across the receiver array are as though the acoustic energy is traveling along the borehole with an apparent velocity equal to the shear wave velocity divided by the cosine of the angle between the direction of the returning wave and the borehole axis.

The numerical simulation shown in FIGS. 13a-13d clearly illustrates the power and utility of the coding scheme when used in conjunction with the system of measurement in FIGS. 12a-12d or FIG. 8. It allows for computer processing of the recorded signals at the receivers to generate correlated records that contain band-limited spike signals with strength proportional to the strength of the non-linear interaction at the mixing zone 1204. The arrival time T of the band-limited spike is equal to the total travel time from source 1201 to mixing zone 1204 and back to the borehole at receiver 1203. The amplitude of the band-limited spikes vary with the receiver position with a maximum occurring at a particular receiver, the location of which is dependent on the scattering angle ψ 1206 of the non-linear interaction at mixing zone 1204. The scattering angle ψ is dependent on the properties of the rocks, e.g. Vp/Vs velocity ratio, at the mixing zone 1204. It should be noted that this result is a characteristic of the coding scheme and of the measurement system shown in FIG. 12a-12d or FIG. 8. The use of Gaussian envelopes and coded signals in conjunction with templates are non-limiting examples used for the purpose of illustrating the coding scheme and its characteristics. Variants of $u_1$, $u_2$ and $u_s$ can be considered in order to optimize the performance of the correlation process in term of resolution and signal to noise ratio in response to various considerations imposed by field applications.

In some aspects of the present disclosure, coded acoustic signals in the primary acoustic beam can also be used to enhance the amplitude and focusing of the non-linear signal returning to the borehole, and to improve signal detection sensitivity and signal to noise ratio. FIGS. 14a-14d show an example of an application of the coded signal scheme to a noisy time series signal generated by numerical simulation. The noisy times series signal simulates a signal returning to the borehole as a result of non-linear interaction. White Gaussian noise with an amplitude 10% larger than the amplitude of the non-linear interaction signal is added to the time-series signal produced by the numerical simulation of wave propagation in a non-linear model before the correlation with the coding template is applied. The configuration is the same as that shown in FIGS. 12a-12d and FIGS. 13a-13d. FIG. 14(*b*) shows the simulated receiving signal containing noise recorded at 6 receivers of the receiver array 1403. FIG. 14(*d*) shows the signal retrieved from the noisy signals (in this case the simulated noisy signals) on the same receivers when correlating with the coded template $u_s$ (t) of 12 pulses shown in FIG. 14(*c*). The coding scheme is thus shown to effectively extract the signal from the non-linear interaction and minimize the noise, a useful characteristic for field applications.

The preceding text described how a combination of broadcast coding and signal processing may be used to improve the detection and to determine the amplitude of an acoustic wave signal generated by non-collinear mixing in a non-linear medium and to determine the acoustic travel time from sources to receiver array via the mixing zone and to infer the mixing zone's non-linearity and Vp/Vs ratio. The following paragraphs describe a non-limiting implementation of the coding and signal processing method in the context of a borehole based measurement system.

Given an initial compressional and shear velocity model of the formations around the borehole, techniques such as ray tracing may be used to estimate the location of a mixing zone,

805 on FIG. 8, corresponding to chosen inclinations and azimuths ($\alpha_1$, $\alpha_2$, $\phi_1$ and $\phi_2$, 809 to 812) and also the convergence and scattering angles ($\theta$ and $\psi$, 804 and 806). This information is used to predict the time delay $\delta_P$ and frequency ratio $d_P$ required for the pulses from the two transmitters to arrive simultaneously at the mixing zone and generate a sequence of scattered pulses by non-collinear interaction that arrive at a receiver, and to predict the total travel time $T_P$ from the first acoustic source to a receiver via the mixing zone. Systematically scanning S and d around their predicted values, and correlating the template $u_s(t)$ with the recorded signal $u_3(t)$ results in a suite of results M (t, $\delta$, d) for each receiver element of the array 803. As discussed in previous paragraphs, the correlated signal M (t, $\delta$, d) for each receiver element contains a band-limited spike corresponding to the non-linear interaction in the mixing zone 805 if selection rules permit non-linear interaction. A search is made in the space of (t, $\delta$, d) on M(t, $\delta$, d) to identify the location ($T_{NL}$, $\delta_{NL}$, $d_{NL}$) of the band-limited spike corresponding to non-linear interaction at mixing zone 805, which should be in the vicinity of ($T_P$, $\delta_P$, $d_P$). Differences between ($T_{NL}$, $\delta_{NL}$, $d_{NL}$) and ($T_P$, $\delta_P$, $d_P$) are indications of deviation of the propagation velocity model from the true propagation characteristics of the rock formation. These differences are then used to update the propagation velocity model by velocity tomographic inversion or other velocity updating methods. Given the relationships between frequency ratio d, Vp/Vs ratio, convergence angle and scattering angle from equation 9 and FIG. 10, the Vp/Vs ratio of the rock formation at the mixing zone is then calculated from the observed value $d_{NL}$, the convergence angle and the scattering angle at the mixing zone—the latter two quantities can be calculated by raytracing or other numerical methods from the updated propagation velocity model. The amplitude value M ($T_{NL}$, $\delta_{NL}$, $d_{NL}$) contains information about the non-linear mixing strength of the rock formation at the mixing zone 805. It can be used for 3D-imaging of non-linear properties of the rock formation as described in the discussion below.

The ability to process non-collinear acoustic mixing signals by correlation with a template signal to identify the combination of parameters associated with a particular mixing zone, that is M ($T_{NL}$, $\delta_{NL}$, $d_{NL}$), $T_{NL}$, $\delta_{NL}$ and $d_{NL}$, that can be subsequently used for the determination of Vp/Vs ratio, propagation model Vp and Vs and nonlinear properties is a direct consequence of the coding and correlating protocol. This unique characteristic underpins the imaging scheme that follows.

The discussion in the paragraphs below will focus on one non-limiting example of the use of coded acoustic signals for creation of the 3D images of Vp/Vs ratio and non-linear properties of rock formation surrounding the borehole. However, the use of coded acoustic signals has broader applications beyond those related to geology and petrophysical applications including the areas of non-destructive testing and medical imaging.

By way of a non-limiting example, one measurement and data processing protocol to enhance signal to noise ratio is discussed in the following paragraphs for the system described in FIG. 8.

For the sake of simplicity, the operating protocol is described in the context of a non-attenuative rock formation. However, the following measurement and data processing protocol can equally be applied to an attenuative rock formation. The effect of attenuation in the rock formation is to displace the origin of the scattered wave by a predictable amount related to the formation Q.

First, for a given ratio frequency ratio d of the two coded signals as described in the above paragraphs, the coded primary acoustic beam signals from first acoustic energy source 801 and second acoustic energy source 802 of the measurement system described in FIG. 8 are transmitted into the earth. A time delay $\delta$ is maintained between two coded signals of source 801 and source 802. The measurement geometry honors the selection rules, and the time delay is such that energy from the two sources arrives substantially simultaneously at the mixing zone. In one embodiment, each component of the three component geophone at receiver 803 at location z3 detects and records the returning acoustic waves. This measurement is denoted m(t, $\delta$, d, z3). Alternatively or in addition a hydrophone may also be provided to detect a pressure signal in the returning acoustic waves.

Second, the coded primary acoustic signals are transmitted from the first and the second acoustic energy sources as described in the above paragraphs but with polarity reversed, that is, with the phase shifted by 180 degrees. The signal recorded at receiver 803 is denoted m_(t, $\delta$, d, z3).

Third, the two signals m(t, $\delta$, d, z3) and m_(t, $\delta$, d, z3) are added together to form the combined signal, which can be denoted as mm(t, $\delta$, d, z3). Because the signals m(t, $\delta$, d, z3) and m_(t, $\delta$, d, z3) have opposite polarity, signals from linear interaction in the rock formation will be cancelled out by the addition of m(t, $\delta$, d, z3) and m_(t, $\delta$, d, z3). However, the non-linear responses of the earth will add coherently since the amplitude of the non-linear responses is proportional to the product of the amplitudes of the two primary signals and therefore will not reverse polarity when the polarity of both primary signals is reversed. Therefore, mm(t, $\delta$, d, z3) would essentially contain a signal from non-linear interaction of the rock formation.

Fourth, a time variant band-pass filter can be applied on the obtained signal mm(t, $\delta$, d, z3), so as to keep a narrow band around the expected bandwidth of the signal. The bandwidth of the obtained signal is determined from the frequency differences and bandwidths of the two primary broadcast signals.

Fifth, a cross-correlation of the filtered signal mm(t, $\delta$, d, z3) with the template coded signal is performed as described in the above paragraphs to obtain the pulsed signal which can be denoted as mmc(t, $\delta$, d, z3).

Sixth, hodogram analysis can be applied to the three component data obtained from the three uniaxial sensors of the receiver and/or applied to the pressure signal detected by the hydrophone. These data may be used to analyze any of the possible modes P, SH and SV and can be transformed to obtain separate measurements of any SV, SH and P arrivals, denoted mmcr(t, $\delta$, d, z3).

Seventh, the above six steps can be repeated multiple times with different broadcast coded signals and the collection of mmcr(t, $\delta$, d, z3) signals can be stacked to improve signal to noise. The resulting stacked signal is the signal record M(t, $\delta$, d, z3) for each of the SV, SH and P arrivals. For example, in a P+P to SV mode, the SV mode is detected by the receiver while in a P+SV to P mode, the detected signal at the receiver would be a P mode.

Eighth, the above seven steps can be repeated for a sweep through for a sequence of many values $\delta$ and d to obtain the entire set of M(t, $\delta$, d, z3). The described measurement and processing protocol allow for the construction of the measurement signals M(t, $\delta$, d, z3) with high signal to noise ratio at the receiver arrays.

The measurements M (t, $\delta$, d, z3) can be repeated for many transmitter locations z1, z2 and many receiver array locations as the transmitter arrays and the receiver arrays can be moved independently. As the primary acoustic beams from source 801 and 802 can be steered independently for any azimuth angles $\phi1$, $\phi2$ and elevation angles $\alpha1$, $\alpha2$, the measurements M(t, δ, d, z3) are also repeated for many angles $\phi1$, $\phi2$, $\alpha1$ and $\alpha2$. These repeated and multiple measurements may contain multiple redundant signals generated by non-linear interactions in the earth for many values of z1, z2, z3, $\phi1$, $\phi2$, $\alpha1$ and $\alpha2$. The redundancy allows for additional signal to noise enhancements by signal processing on computers and for creation of 3D images of rock properties around the borehole.

It should be noted that the steps described above for the measurement and processing protocol can be re-ordered or eliminated in various permutations as warranted. Furthermore, there are many additional signal processing techniques familiar to those who are experienced with the art of seismic signal processing, e.g. multi-dimensional filtering, time moveout analysis and stacking. These additional techniques can be added to the measurement and data processing protocol described in the above paragraphs to improve the quality of the recorded data and processed images. The correlated acoustic signal M(t, δ, d, z3) from non-linear interactions has many properties rooted in the coding methodology and the selection rules.

In the following paragraphs, an imaging method and workflow that exploits these properties to construct 3D images of the non-linear properties and Vp/Vs velocity ratio of an earth volume and determines other rock properties such as Vp and Vs is discussed. A non limiting example of the workflow is discussed below.

Referring to the measurement system described in FIG. 8 with travel time notations denoted in FIGS. 12a-12d, and the discussion in the above paragraphs, the correlated signal record M (t, δ, d, z3) after measurement and processing at a receiver location z3 for one particular transmitter location and beam angle (z1, z2, $\phi1$, $\phi2$, $\alpha1$ and $\alpha2$) will contain a band-limited spike at the travel time T=t1+t3 if the following conditions are satisfied:
 a) The transmitted beams intersect and interact non-linearly at mixing zone 805.
 b) The time difference δ is equal to the travel time difference t1−t2.
 c) The selection rules are obeyed, i.e., the frequency ratio d used in the coding scheme obeys the condition of equation (9).

$$\sin(\theta/2) = (1-d)\frac{\sqrt{(Vp/Vs)^2 - 1}}{2\sqrt{d}} \quad (19)$$

where Vp/Vs is the compressional to shear velocity ratio at the mixing zone 805 and θ is the convergence angle between the first and second transmitted beams. The Vp/Vs ratio and convergence angle θ can be calculated by raytracing from the beam geometry, location and beam direction parameters (z1, z2, z3, $\phi1$, $\phi2$, $\alpha1$ and $\alpha2$) and a model of compressional velocity Vp and shear velocity Vs of the rock volume being investigated.

The above conditions dictate that the non-linear interaction at mixing zone 805 contributes to the record M (t, δ, d, z3) as a band-limited spike signal at a single point in the (t, δ, d) space for each position z3 of receiver 803. The observed location of the band-limited spike signal on the record M (t, δ, d, z3) can be denoted as ($T_{NL}$, $\delta_{NL}$, $d_{NL}$, z3). The amplitude of this band-limited spike is a function of the non-linear interaction strength, β, at mixing zone 805.

A combining process (e.g., a stacking process) as commonly used in the seismic industry and borehole acoustic waveform analysis can be performed on the signal records M (t, δ, d, z3). The progressive time delay or "moveout" of the band-limited spikes on the signal records M (t, δ, d, z3) can be analyzed as a function of z3. For example, in a stacking process, the signal records can be stacked to obtain a stacked record Ms(t, δ, d, z3r) corresponding to a chosen reference location z3r. The reference location is selected such that the plurality of signal records M (t, δ, d, z3) can be stacked appropriately. This stacking process enhances the signal to noise ratio and improves the detectability of the location ($T_{NL}$, $\delta_{NL}$, $d_{NL}$, z3r) of the band-limited spike originating from the non-linear interaction on the record M s(t, δ, d, z3r). Although a stacking process is described herein, other combination techniques can also be used.

Given an initial Vp and Vs velocity model, which can be estimated from the borehole well logs and assumptions about lateral continuity of the rock formation properties away from the borehole, the trajectories and travel times of acoustic beams with elevation angle $\alpha1$ and azimuth angle $\phi1$ from transmitter 801 at position z1 and elevation angle $\alpha2$ and azimuth angle $\phi2$ from transmitter 802 at position z2 can be calculated by ray tracing or other numerical modeling techniques.

Therefore, the location of the mixing zone 805 can be located in space by ray tracing or other acoustic numerical modeling techniques from the parameters z1, z2, z3r, $\phi1$, $\phi2$, $\alpha1$ and $\alpha2$ if the beams intersect. The predicted travel time t1p, t2p and t3p between transmitter locations 801 and 802, reference receiver z3r and mixing zone 805 can also be calculated based on position and velocity using ray tracing or other acoustic numerical modeling techniques.

The predicted pulse arrival time $T_P$=t1p+t3p and time difference $\delta_P$=t1p−t2p can be predicted from the compressional velocity Vp and shear velocity Vs model and then compared with the arrival time $T_{NL}$ and difference time $\delta_{NL}$ of the observed band-limited spike on the actual record Ms(t, δ, d, z3r). If the Vp and Vs velocity model correctly approximates the true Vp and Vs velocity of the rock formation, the predicted times ($T_P$, $\delta_P$) are equal to observation times ($T_{NL}$, $\delta_{NL}$). If there are differences between the predicted times and the observed times, these differences can be used to update the propagating Vp and Vs velocity model to minimize the differences and achieve consistency between the modeled and observed data. Various iterative velocity tomographic inversion methods that are familiar to those experienced in the art of imaging in the seismic processing industry can be used to update the propagating Vp and Vs model.

Given the Vp and Vs propagation model obtained through the above tomographic velocity inversion step, the trajectories of acoustic beams with elevation angle $\alpha1$ and azimuth angle $\phi1$ from transmitter 801 at position z1 and elevation angle $\alpha2$ and azimuth angle $\phi2$ from transmitter 802 at position z2 can be calculated by ray tracing or other numerical modeling techniques For a given azimuth angle $\phi1$, there will be an azimuth angle $\phi2$ for which the source beams will intersect at a mixing zone 805 for which the location and convergence angle θ can be calculated by ray tracing or other numerical modeling techniques from the parameters z1, z2, z3r, $\phi1$, $\phi2$, $\alpha1$ and $\alpha2$. The amplitude of the pulse at the point ($T_{NL}$, $\delta_{NL}$, $d_{NL}$) on the record Ms(t, δ, d, z3r) can then be mapped to the spatial coordinates of the mixing zone 805. Since $d_{NL}$ must obey Equation (19), the Vp/Vs velocity ratio at the mixing zone 805 can be calculated from Equation (19) and mapped on to its spatial position. By repeating the above mapping step for a range of values of parameters z1, z2, z3, φ1, φ2, α1 and α2, a 3D image of the non-linear interaction. strength β and a 3D image of velocity ratio Vp/Vs can be constructed. The velocity Vp/Vs ratio obtained from the above mapping method using selection rules is an alternative method to using the ratio of the propagation velocity Vp and Vs obtained from tomographic inversion of travel times.

The geometric mapping step discussed in the above paragraphs is only one example of many imaging techniques that can be used for 3D imaging for non-linear property and Vp/Vs velocity ratio from the signal records M (t, δ, d, z3) for many values of parameters z1, z2, φ1, φ2, α1 and α2. Other advanced imaging techniques such as Kirchhoff imaging, beam imaging, wave equation imaging used in the seismic industry can be adapted for the 3D imaging of non-linear property and Vp/Vs velocity ratio. For example, the three dimensional image of the propagation compressional velocity Vp, the three dimensional image of the propagation of shear velocity Vs, the three dimensional image of the ratio of compressional velocity and shear velocity Vp/Vs, or the three dimensional image of non-linear properties of a rock formation, or any combination of two or more thereof can be performed using Kirchhoff imaging, beam imaging or wave equation imaging. In addition, in one embodiment, the value of propagation compressional velocity or value of shear velocity or both can also be determined using tomographic velocity inversion or full wave form inversion or by iterative imaging in combination with tomographic velocity inversion or full wave form inversion.

As it can be appreciated, determining a value of a parameter can be different from imaging the parameter. Indeed, an image of a parameter may only contain relative values of the parameter and does not necessarily provide the information on the absolute value of the parameter. Therefore, obtaining an image of the velocity ratio Vp/Vs may be different from determining the value of the velocity ratio Vp/Vs. Determining a value of the velocity ratio from the image of the velocity ratio may require additional information.

For investigation of non-linear properties and the ratio of compressional to shear velocities farther into the rock formation from a borehole, sources of lower frequency, of order 500 Hz to 10 khz, may be needed since acoustic energy of lower frequency can penetrate farther into the rock formations before being attenuated to a non-detectable level. Lower frequency acoustic energy in the 500 Hz to 10 kHz frequency range has a wavelength much bigger than the borehole diameter. In these circumstances it is difficult to control the azimuth directions of the acoustic wave broadcast from sources deployed in the borehole. The configuration shown in FIG. 8 with two primary beams of acoustic energy emanating from a borehole may not be suitable for probing and imaging of non-linear properties at large distance greater than hundreds of feet from the borehole. In view of this, a different low frequency (500 Hz to 10 kHz) system and method is needed to maximize the distance of investigation away from the borehole. The following paragraphs describe a non-limiting example of such a system and method to generate three-dimensional images of non-linear acoustic properties and Vp/Vs velocity ratio using low frequency sources. Although the following description will refer to the frequency range 500 Hz to 10 kHz, the system and method described can also be applicable and beneficial in a higher frequency ranges, for example, 10 kHz to 500 kHz.

FIG. 15a shows a system of two transmitters and a receiver or a receiver array that are arranged in the borehole to detect non-collinear mixing in a rock volume around the borehole. In one embodiment, the upper transmitter 1502 includes a linear array of transmitters which can be clamped to or unclamped from the borehole. The lower transmitter 1501 includes a linear array of transmitters which can also be clamped or unclamped. The receiver array 1508 includes a clamped three component receiver or a clamped three component receiver array. The transmitters and receivers can be moved together or independently. In one embodiment, array elements of transmitters 1501 and 1502 can be arranged, for example using phase control, to broadcast acoustic energy into two cones (lower acoustic cone 1504 produced by transmitter 1501 and upper acoustic cone 1505 produced by transmitter 1502), with axes collinear with transmitters 1501 and 1502. In a phase controlled system, the cone angles depend on the phase difference between transmitter elements and the rock formation velocity. The intersection of the two conical broadcasts of acoustic energy is a toroidal shaped intersection volume 1506. Where the selection rules are honored, scattered energy 1507 is generated by non-linear interaction around intersection volume center 1506. The scattered energy originating from non-linear interaction is recorded at the receiver or array of receivers 1508.

Because the vertical locations and the elevation angles of the conical broadcasts of the transmitters 1501 and 1502 are controllable, the spatial location (distance from the borehole and vertical location) of their toroidal intersection volume 1506 may be controlled and scanned over a three dimensional rock volume around the borehole 1500. To the extent that the convergence angles of the two cones and the frequency ratios of the two sources can be arranged to honor the selection rules, the scattered signals due to non-linear mixing at mixing zone 1506 that are recorded at receiver 1508 contain information of the non-linear properties of the formation at the intersection between the two cones. The data recorded by an array of three component geophones 1508 may be analyzed to determine the azimuth and elevation to its origin. The signal coding methodology described in the above paragraphs and the measurement and processing protocol described above can be applied to the system depicted in FIG. 15(a). The correlated signal M (t, δ, d, z3) obtained from the latter system and configuration is composed of the linear superposition of all the pulses generated by the non-linear interaction at all intersection volume segments 1509-1, 2, 3, etc. to 1509-k, that cover the entire circumference of the toroid intersection volume 1506 as shown in FIG. 15(b). As discussed in the above paragraphs, the contribution of the non-linear interaction of the wave by a segment 1509-k, corresponding to the interaction or mixing zone, to the resulting correlated signal M (t, δ, d, z3) at a receiver at position z3 in receiver array 1508 is a pulse with a travel time equal to the time of flight from transmitter 1501 to segment 1509-k and from 1509-k to receiver if the following conditions are met:

a) the frequency ratio d, convergence angle θ and Vp/Vs velocity ratio at the particular segment 1506-k obeys the selection rule condition of equation (19), b) the time delay S between the coded source transmitters signals is equal to the difference between the times of flight from transmitter 1501 to 1509-k and from transmitter 1502 to 1509-k.

In other words, the pulses generated by non-linear mixing at the intersection volume segments 1509-1 to 1509-k in the correlated signal M (t, δ, d, z3) are distributed over a range of (t, δ, d) for each receiver at position z3. The contribution of each segment 1509-k can be mapped to a point in (t, δ, d) space in the correlated signal M(t, δ, d, z3). This property, together with the trajectory information of the signal obtained from three component receivers allows for geometric mapping of the signal amplitude at the point (t, δ, d) in correlated signal M (t, δ, d, z3) to the spatial locations of the intersection volume segments 1509-1 to 1509-$k$ within the toroid intersection volume using the imaging methods discussed in the above paragraphs. An initial Vp and Vs propagation model is constructed. Ray tracing, travel time analysis and iterative tomographic velocity determination are then performed to obtain an updated Vp and Vs propagation model. Non-linear properties and Vp/Vs velocity ratio in the segments 1509-1 to 1509-$k$ in the toroid intersection volume can then be extracted and mapped to the spatial locations on the toroidal intersection volume using ray tracing analysis applied to the updated Vp and Vs model using the workflow described in the above paragraphs. By repeating the measurements for all elevation angles of conical broadcast and vertical locations in the borehole of the transmitters, the images of non-linear properties and Vp/Vs velocity ratio can be constructed for all mixing zones surrounding the borehole. The images for all scanned mixing zones can then be combined to yield a complete 3D image of non-linear properties and Vp/Vs velocity ratio using a suitable processing method known to those who are skilled in the art of seismic imaging such as, for example, the weighted stacking method, of all the images.

The system and method using low frequency conical acoustic broadcasts for a vertical well can work well when the rock volume has no azimuthal symmetry. However, if the rock volume has a very high degree of azimuthal symmetry for the propagating velocities Vp and Vs and therefore by implication their Vp/Vs velocity ratio, such a system may encounter some difficulties in resolving the azimuthal variations in formation properties and generating 3D images. Referring to FIG. 15(*b*), the non-linear signals generated by non-linear interaction from segments 1509-1 to 1509-$K$ in the toroid intersection volume arrive simultaneously at each receiver when there is total azimuthal symmetry. In this case, it would be difficult to separate the pulses originating from multiple segments 1509-1 to 1509-K in the toroidal intersection volume as these occur at the same time in the correlated signal M. This introduces ambiguity into the mapping exercise. The above difficulty can be avoided if a borehole or borehole system is designed to overcome the limitations due to the azimuthal symmetry. In the following paragraphs, a non-limiting measurement system and method utilizing various wellbore configurations designed to achieve this goal will be described.

Figure 16B:
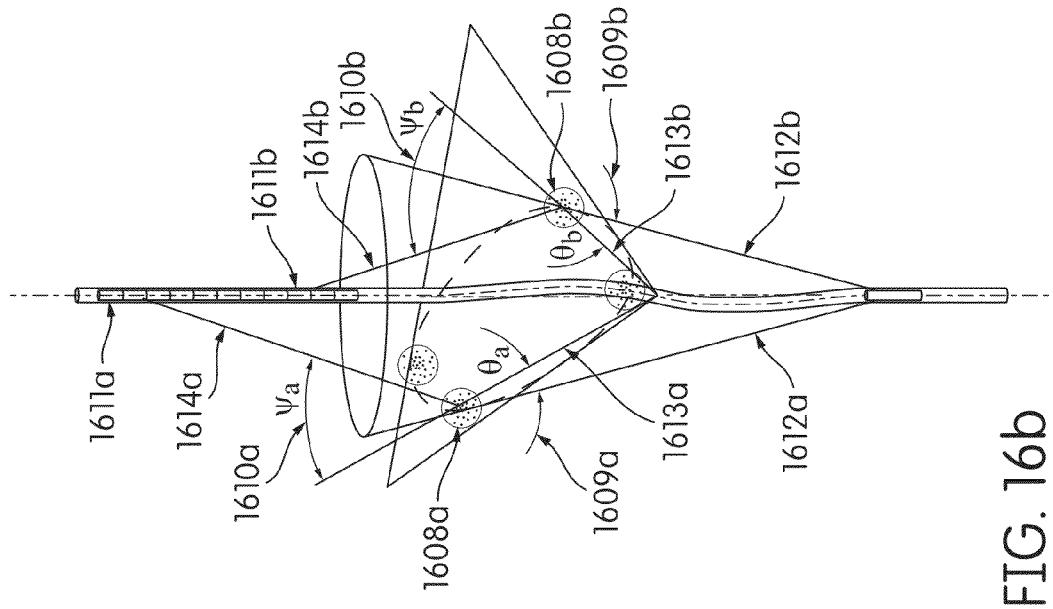
FIGS. 16a and 16b show an example non-collinear mixing arrangement between two intersecting coaxial cones, in accordance with aspects of the present disclosure.
Figure 16A:
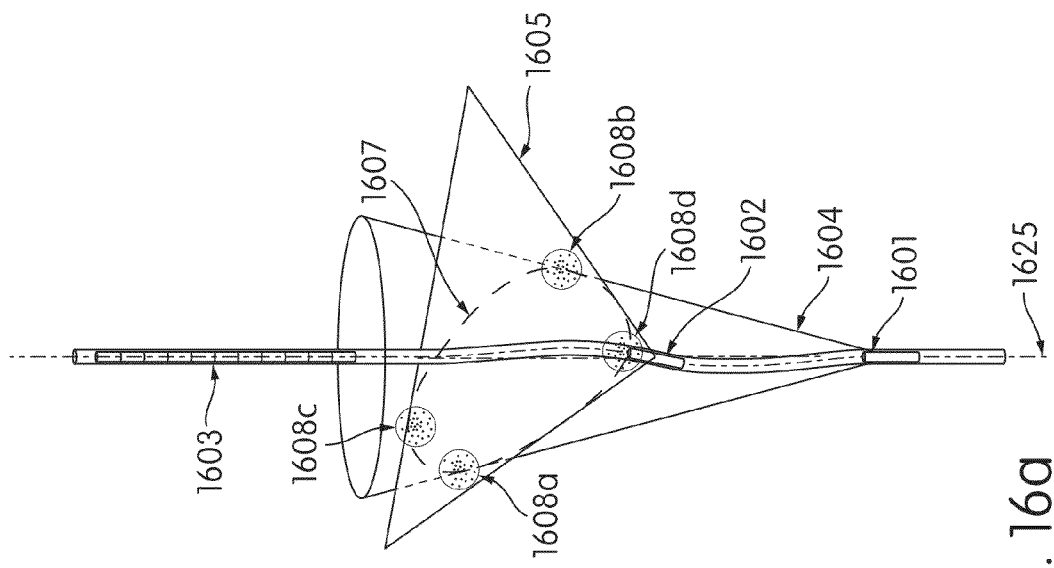

FIGS. 16*a* and 16*b* show an example of non-collinear mixing arrangement with receiver array 1603 located in a straight section of the borehole and centers of transmitters 1601 and 1602 located on the receiver array's extended axis 1625. For the case of linear phased arrays, the transmitters broadcast acoustic energy in cones 1604 and 1605 with axes aligned with the transmitter arrays. The cones and their intersection locus 1607 are illustrated in FIGS. 16*a* and 16*b*, in accordance with aspects of the present disclosure. As shown in FIG. 16*a*, the intersection locus may be considered as a series of adjacent intersection volume segments, 1608-$k$, where k=1 to K, four of which are identified as 1608*a*, 1608*b*, 1608*c* and 1608*d*. From geometric analysis it can be demonstrated that if two intersection volume segments have the same convergence angles, their corresponding time of flight differences (from lower and upper transmitter to intersection volume segment) t1–t2 are different. Two locations on opposite sides of the intersection locus corresponding to the mixing zones, with similar convergence angles and Vp/Vs velocity ratio, may therefore be individually activated by controlling the frequency ratio d and the time delay δ between coded broadcasts from the two transmitters. Similarly, two mixing zones with the same time of flight difference t1–t2 have different convergence angles θ, so that an acoustic signal arriving simultaneously at two mixing segments could only honor the selection rule requirements for a Vp/Vs velocity ratio, frequency ratio d and convergence angle θ at one of the two locations.

As it can be appreciated from the above paragraphs, the intersection of two conical acoustic broadcasts defines an intersection volume in a form of a toroid. For the purpose of the present disclosure, a toroid is defined as an "annular" shape that is generated by revolving a plane geometrical shape such as a polygonal shape, circle, ellipse or other shape to define a closed volume. In one embodiment, the toroid can be a ring torus or O-ring where the plane geometrical shape or cross-sectional shape is a circle that is revolved around an axis. In another embodiment, the toroid can be defined as a polygonal shape that is revolved elliptically to form a closed volume. The toroid volume can be segmented in to a plurality of intersection volume segments. Depending upon non-linear selection rules and a judicious selection of various parameters including a start time difference and frequency ratio between the broadcast acoustic signals, one a more intersection volume segments can be "activated" to provide one or more mixing zones where the two conical broadcast signals interact non-linearly within the mixing zone(s) to generate a signal that is representative of the non-linear properties of the rock formation in that zone.

The coding methods discussed in the above paragraphs, the measurement and processing protocols described in the above paragraphs and the imaging methods discussed in the above paragraphs can be applied to the measurement system illustrated in FIGS. 16*a* and 16*b*. The applications follow the general approach described in the above paragraphs. Unlike the straight borehole configuration of FIG. 15, there is no issue of simultaneous arrivals in the space of (t, δ, d). Thus, measurement system described in FIG. 16 using a borehole with an intentionally bent trajectory would be more robust for general 3D imaging of non-linear properties and Vp/Vs velocity ratio. A by-product of the imaging method is the Vp and Vs propagation model generated by tomographic velocity inversion of the intermediate step of the imaging process.

It should be noted that the absence of azimuthal symmetry in the configuration of the curved or angled borehole trajectory and tilted conical acoustic wave broadcast as shown on FIG. 16 can also be achieved on a smaller scale by offsetting the axes of smaller transmitter arrays within a straight borehole, or by a similar configuration on a wireline or pipe conveyed logging tool, etc.

Figure 17B:
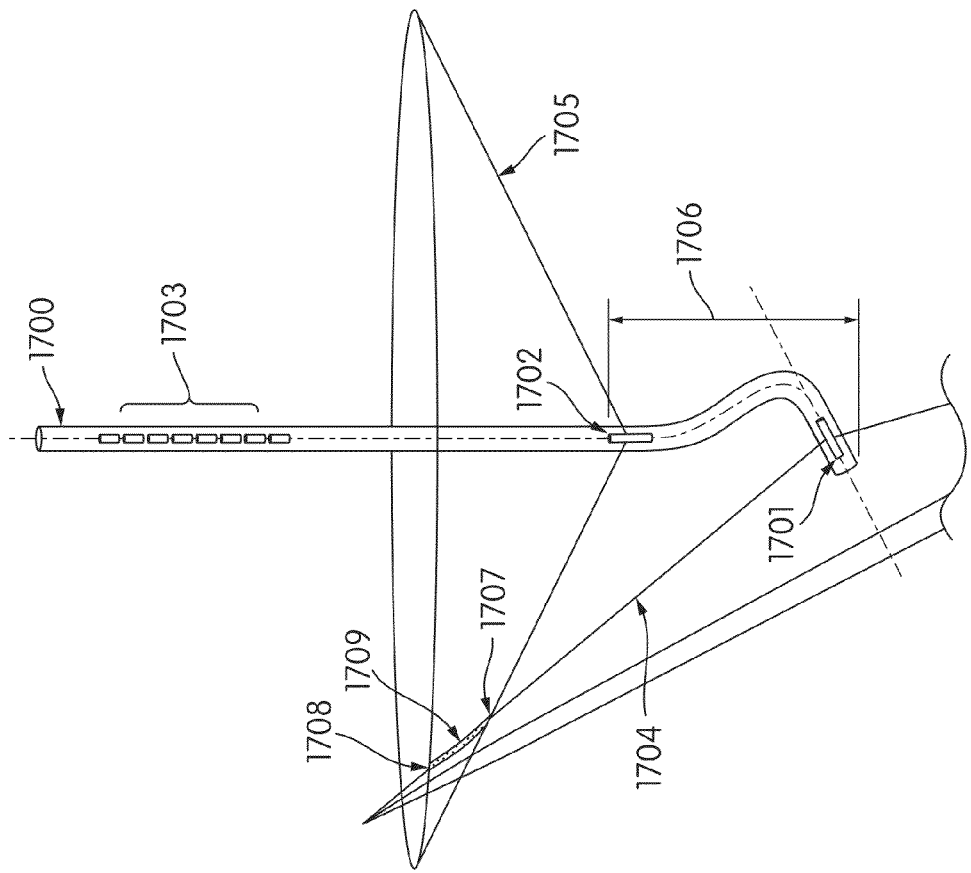
FIG. 17b shows another example single well arrangement with a cranked rathole where a lower transmitter emits energy near perpendicular to a borehole axis, in accordance with aspects of the present disclosure.
Figure 17A:
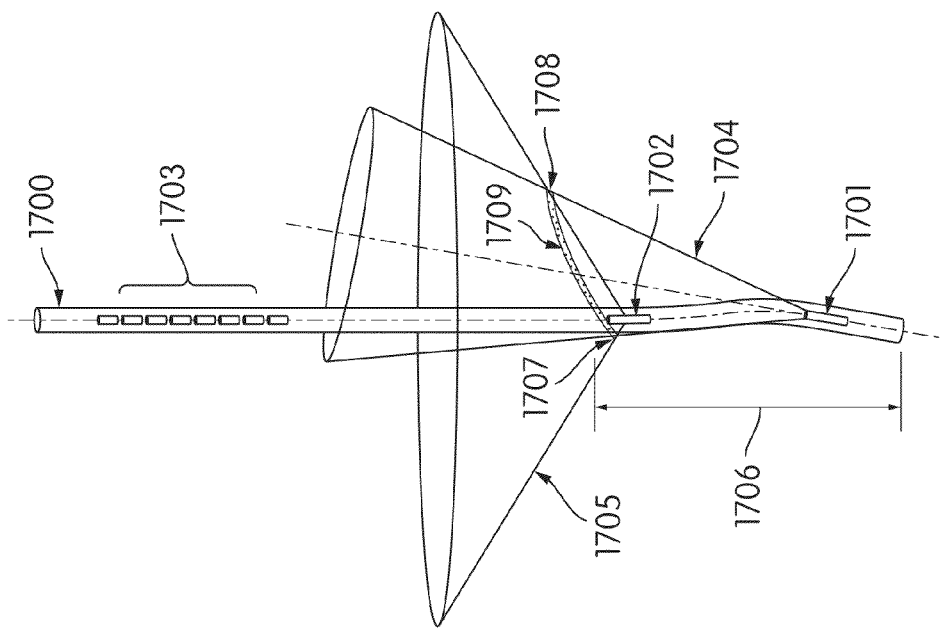
FIG. 17a shows an example single well arrangement with a cranked rathole where there is a complete intersection of lower cone with upper cone, in accordance with aspects of the present disclosure.

FIGS. 17*a* and 17*b* show two additional examples of transmitter-receiver arrangements within various boreholes configurations of axial orientation and cone angle that can be used for the creation of the 3D images of Vp/Vs velocity ratio and non-linear properties of rock formation surrounding the borehole. FIG. 17*a* shows an example single well arrangement with a cranked rat hole where there is a complete intersection of lower cone within the upper cone. For example, as shown in FIG. 17*a*, upper transmitter 1702 is arranged to produce a wider cone of acoustic energy 1705 than the narrower cone 1704 produced by lower transmitter 1701, such that there is a complete intersection of the lower cone within the upper cone. Both transmitters 1701 and 1702 are positioned in rat hole 1706, while receiver 1703 is positioned in main vertical borehole 1700. As in the configurations of FIGS. 15 and 16*a*-16*d*, transmitters 1701 and 1702 can be arranged as an array, for example a linear array, of acoustic point sources in a borehole. Acoustic energy generated by transmitters 1701 and 1702 interacts in the non-linear material in the intersection zone and acoustic energy is received at receiver 1703 in accordance with the selection rules, as discussed above. The non-linear mixing zone includes an intersection locus 1709 between cones 1704 and 1705 spanning a closest point 1707 to the borehole 1700 and a farthest point 1708 from the borehole 1700.

FIG. 17b shows another example of single well arrangement with a more severely cranked rat hole with a lower transmitter emitting energy near perpendicular to the axis of borehole 1700. In these configurations, the intersection between the cones is a hyperbola, not an ellipse as in the above examples. Nonetheless, similar measurements, coding, data processing and imaging protocols remain applicable. In addition, because the intersection between the cones is not a closed curve, depth of investigation is determined by source strength, receiver sensitivity, and the effectiveness of the signal processing algorithms.

One difference between a configuration resulting in a closed elliptical intersection locus with a configuration resulting in a parabolic open curve locus is that in a closed elliptical intersection locus a frequency ratio scan may start at a low frequency ratio f2/f1 (see, for example, FIG. 10b) that corresponds to a convergence angle higher than that at the nearest point. The frequency ratio f2/f1 can then be increased, for example, until the nearest point on the ellipse is activated. The scan can be continued until the farthest intersection point is reached. By increasing further frequency ratio f2/f1 no signal would be received as no zone is activated. On the other hand, if the intersection is an open curve, the frequency ratio f2/f1 can be scanned starting at the nearest point and continue until the returning signals to the receiver from either side of the hyperbola become undetectable.

FIG. 18a shows an example of a vertical well and sidetrack with receivers in the vertical part of the well. FIG. 18b shows another example of a vertical pilot hole and horizontal sidetrack with receivers in the sidetrack in accordance with aspects of the present disclosure. The main vertical borehole 1800 includes transmitter 1801 arranged to produce a vertical cone of acoustic energy 1804, while sidetrack borehole 1806 includes transmitter 1802 arranged to produce acoustic cone 1805. Receiver 1803 can be arranged in either main vertical borehole 1800 as in FIG. 18a, sidetrack borehole 1806 or both main borehole 1800 and sidetrack borehole 1806 depending on the particular application used. As in the examples of FIGS. 17a to 17c, transmitters 1801 and 1802 and receiver 1803 can include an array of transmitters and receivers, respectively. Transmitter 1802 in sidetrack borehole 1806 can be located above or below transmitter 1801 in main vertical borehole 1800.

Although the configurations of FIGS. 17a to and 17b, 18a and 18b differ somewhat in complexity from the drilling and operation perspectives, there are many benefits to using different configurations including the ability to perform deeper remote sensing from the borehole by maximizing the distance to the intersection of the two cones. Moreover, transmitters generating acoustic energy in a direction near perpendicular to the borehole can provide more power and more angular resolution for the scans defined by smaller cone angles. It should be noted that the above Figures are only example configurations of the use of a multitude of possible borehole configurations. As it can be appreciated, there are many other borehole configurations that also allow for the placement of the two primary acoustic arrays at different azimuth angles and elevation angles.

The techniques described above, a combination of invoking the selection rules and signal coding, may be used to scan and image a volume defined by two intersecting cones formed by the acoustic energy from the two transmitters, some distance away from the borehole. The discussion above described the P+P⇒SV interaction. However, other permitted interactions can also be used in a similar fashion with examples shown in Table 1.

Figure 19:
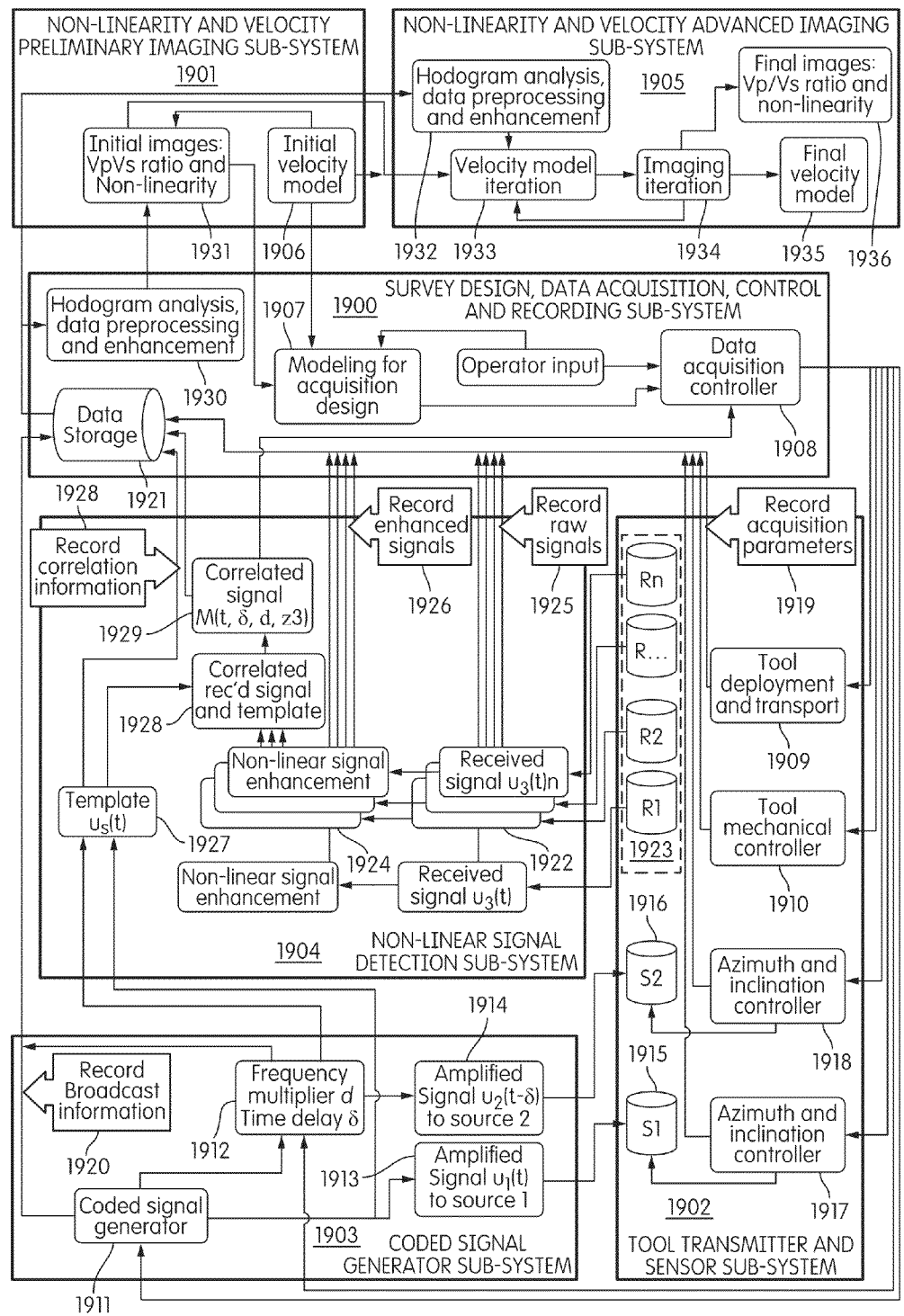
FIG. 19 is a schematic system diagram of a system for performing survey design, data acquisition, data processing and imaging, in accordance with aspects of the present disclosure.

As can be appreciated from the above paragraphs, various methods of investigating a rock formation can be implemented with a system for survey planning, data acquisition and storage, and image processing and interpretation. FIG. 19 depicts a system for survey planning, data acquisition and storage, and image processing and interpretation, according to an embodiment of the present invention. In one embodiment, the system can generate 3D images of non-linearity properties, Vp/Vs velocity ratio and propagation compression and shear velocity of a cylindrical volume of rock formation, centered on the wellbore. In one embodiment, the 3D images of non-linearity and Vp/Vs velocity ratio can include images of non-linearity and Vp/Vs velocity ratio extending out to a radius of investigation of several hundred meters, for example.

In one embodiment, the system may be considered as a suite of hardware and/or software or module sub-systems. Sub-systems 1900 to 1904 are used for survey planning and execution, downhole tool conveyance, coding and broadcast of the transmitted acoustic waves, and recording and detection of the non-linear signal. Sub-systems 1901 and 1905 are used for post-survey image processing. Sub-system 1900 is used for survey design, data design acquisition, control and recording. Sub-system 1901 is used for preliminary non-linearity and velocity imaging. Sub-system 1902 is used for receiver and sensor control and transmission. Sub-system 1902 is configured to emit controlled acoustic broadcasts and receive acoustic energy. Sub-system 1903 is used for generating a broadcast signal. Sub-system 1904 is used for non-linear signal detection. Sub-system 1905 is used for imaging non-linearity and imaging velocity.

In one embodiment, sub-system 1900 includes modeling for acquisition module 1907, data acquisition controller 1908, data pre-processing and enhancement module 1930 and data storage device 1921. In one embodiment, sub-system 1901 includes initial velocity model module 1906 and module 1931 for preliminary generation of three dimensional images including propagation compressional and shear velocity images, Vp/Vs velocity ratio images and images of non-linearity which are associated with amplitudes of the measured signal originating from the non-linear interaction at the mixing zone. In one embodiment, sub-system 1902 includes tool deployment and transport module 1909, tool mechanical controller 1910, azimuth and elevation controller 1917 for controlling the azimuth and elevation angles of the first acoustic source (S1), and azimuth and elevation controller 1918 for controlling the azimuth and elevation angles of the second acoustic source (S2). In one embodiment, sub-system 1903 includes coded signal generator 1911, frequency multiplier and time delay module 1912, signal amplifier 1913 for generating the signal sent to first acoustic source (S1), signal amplifier 1914 for generating the signal sent to second acoustic source (S2). In one embodiment, sub-system 1904 includes receiver module(s) 1922 for receiving signals $u3(t)$ from receivers R1, R2, ... Rn, non-linear signal enhancement module(s) 1924 for enhancing the signal received by the signal receiver module(s) 1922, a template signal generator module 1927 for generating a template signal $u_s(t)$, and a signal correlation module 1928 for correlating the received signal $u_3(t)$ with the template signal $u_s(t)$, as described in the above paragraphs. In one embodiment, sub-system 1905 includes data pre-processing and enhancement module 1932, velocity model iteration module 1933, imaging iteration module 1934, output image module 1936 for velocity ratio images and/or non-linearity images, and output velocity module 1935 for outputting determined values of velocities Vp, velocity Vs and/or Vp/Vs velocity ratio.

As it can be appreciated, the term module is used herein to encompass a hardware device, a software program, or both. For example, image iteration module can be a piece of hardware that is configured to perform the iteration or a software program that can be run on a computer to perform the iteration, or includes both a piece of hardware and software application.

In operation, prior to data acquisition, logs of compressional and shear slowness and information about formation lateral continuity can be used to build an initial layered earth model extending laterally away from the well bore using module 1906. The initial velocity model from module 1906 is used by a forward modeling acquisition module 1907 to provide a plan for data acquisition that an operator uses to program data acquisition controller 1908 using operator inputs.

After sub-system 1902 is deployed into the borehole via tool deployment and transport module 1909 and clamped via tool mechanical controller 1910 to the borehole wall if needed, input commands can be sent to the coded signal generator sub-system 1903 where coded pulse sequences are generated by coded signal generator module 1911. The coded signals generated by the coded signal generator module 1911 are adjusted in frequency and delayed by the frequency multiplier and time delay module 1912 such that the signal amplifiers 1913 and 1914 provide signals to transmitters or sources S1 1915 and S2 1916 to broadcast the signals in a delayed fashion so that the signals from S1 and S2 arrive simultaneously at the mixing zone, as depicted, for example, on FIG. 12*a*.

The geometry of the broadcasts including the elevation and azimuth angles of the acoustic broadcasts from sources S1 1915 and S2 1916 is controlled by commands from the data acquisition controller 1908 which sends angle control commands to downhole azimuth and elevation angle controllers 1917 and 1918. All data pertaining to tool configuration and broadcast geometry collected from tool deployment 1909, tool mechanical controller 1910, azimuth and elevation controllers 1917 and 1918 indicated herein as record acquisition parameters 1919 are recorded data storage device 1921. Similarly, the coding scheme from coded signal generator subsystem 1903 indicated herein as record broadcast information at 1920 is also recorded at data storage device 1921.

In one embodiment, signals from signal modules 1922 recorded at the receiver or receivers 1923 (e.g., each of the receivers may have for example hydrophones, 3 component geophones or both R1 to Rn) can be processed by non-linear signal enhancement module 1924 to enhance the content of non-linear origin and reduce or substantially suppress signals of linear interaction origin or potential noise. Raw signals indicated at 1925 from signal receive modules 1922 and enhanced signals indicated at 1926 are stored in data storage device 1921. A template signal $u_s(t)$ generated by template signal generator 1927, which can be derived from signals $u_1(t)$ and $u_2(t)$ generated by signal generators 1912 and frequency multiplier and time delay module 1912, is correlated with received signals indicated by 1925 at 1928, as described for example in FIGS. 12 to 14. The correlation of template signal $u_s(t)$ and received or detected signal $u_3(t)$ is used to extract via correlated signal output module 1929 a correlated signal $M(t, d, \delta, z3)$. The correlated signal is also stored in data storage device 1921.

In one embodiment, the data acquisition process implemented using components or modules 1909 to 1929 may be repeated with different beam geometry or at a multiple locations (z3) within the well. In one embodiment, data already recorded may be used to guide changes in acquisition parameters. For example, stored data within storage device 1921 may be further enhanced, for example, by hodogram analysis within preprocessing and hodogram processing module 1930. The data stored in storage device 1921 can be further used in conjunction with initial velocity model from initial velocity model module 1906 to create a set of images of non-linear properties and/or Vp/Vs ratios with imaging module 1931. These may be used to refine modeling by acquisition design module 1907 and/or acquisition parameters controlled by data acquisition controller 1908.

After the survey is complete, further data processing may be implemented via data pre-processing and enhancement module 1932. In one embodiment, hodogram analysis can be conducted to pre-condition the data for final analysis. The initial velocity model in module 1906 and images from module 1931 can be used as a starting point for further iteration of the velocity model through velocity model iteration module 1933 and imaging iteration of non-linear properties and/or Vp/Vs ratio through imaging iteration between velocity modeling module 1933 and imaging module 1934. The final result of the iteration is an optimized velocity model output through output module 1935 and images including Vp/Vs ratio images and/or non-linear properties images output through output module 1936.

In one embodiment, the above implementation of the system is suitable for imaging out to relatively large distances from the wellbore (for example out to several hundred meters) and includes components designed to maximize signal to noise ratio and the detection of tenuous signals from a complex petrophysical, stratigraphic and structural context. Near wellbore applications probing a smaller volume with less variation in properties and stronger returned signals could potentially dispense with some aspects or portions or modules of the system concerned with signal detection and velocity model iteration. Likewise, in a less demanding acquisition environment, some aspects of the hardware could be simplified, for example clamped three-component geophones could be replaced with non-directional hydrophone receivers mounted on a centralized sonde.

Furthermore, as it can be appreciated, although the system is described above as linking the acquisition data portion of the system to the imaging portion of the system, the acquisition of data portion can be accomplished separately from the imaging of Vp/Vs ratio and/or non-linear properties. Indeed, the acquired data can be accomplished by a first entity and the data stored in data storage device 1921. The acquired data in data storage device 1921 can then be transferred to a second entity, which can be the same or different from the first entity, the second entity can employ the imaging sub-system or imaging method described in the above paragraphs to obtain the Vp/Vs and/or non-linear properties images.

Furthermore, although each module is described in the above paragraphs as having a specific functionality, as it can be appreciated any functionality in one or more modules can be moved to any other one or more modules. For example, some or all functionality in the coded signal generator subsystem 1903 can be moved to the non-linear signal detection subsystem 1904.

In addition, it must be appreciated that the term processor is used herein to encompass one or more processors. The one or more processors can be configured to implement the methods or portions of the methods described herein. The one or more processors can be located in one or more computers such as, for example, in a distributed computing environment. In some embodiments, programs for performing methods in accordance with embodiments of the invention can be embodied as program products in a computer such as a personal computer or server or in a distributed computing environment comprising a plurality of computers. Where reference is made to a processor that term should be understood to encompass any of these computing arrangements. The computer may include, for example, a desktop computer, a laptop computer, a handheld computing device. The computer program products may include a computer readable medium or storage medium or media having instructions stored thereon used to program a computer to perform the methods described above. Examples of suitable storage medium or media include any type of disk including floppy disks, optical disks, DVDs, CD ROMs, magnetic optical disks, RAMs, EPROMs, EEPROMs, magnetic or optical cards, hard disk, flash card (e.g., a USB flash card), PCMCIA memory card, smart card, or other media. Alternatively, a portion or the whole computer program product can be downloaded from a remote computer or server via a network such as the Internet, an ATM network, a wide area network (WAN) or a local area network.

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims. As a further example, it is to be understood that the present invention contemplates that, to the extent possible, one or more features of any embodiment can be combined with one or more features of any other embodiment.

What is claimed is:

1. A system for investigating rock formation outside a borehole, the system comprising:
    a first acoustic source configured to generate a first acoustic signal at a first frequency;
    a second acoustic source configured to generate a second acoustic signal at a second frequency;
    wherein the first acoustic source and the second acoustic source are arranged and positioned within the borehole and are controllable such that the first and the second acoustic signals intersect in an intersection volume outside the borehole and a start time difference is provided between the second acoustic signal and the first acoustic signal;
    a receiver arranged within the borehole, the receiver being configured to receive a detected signal returning to the borehole having a frequency equal to a difference between the first frequency and the second frequency, the detected signal being generated by a non-linear mixing process from the first acoustic signal and the second acoustic signal in a non-linear mixing zone within the intersection volume; and
    a recording system configured to record the detected signal and store the detected signal in a storage device and to record measurement parameters including a position of the first acoustic source, a position of the second acoustic source, a position of the receiver, elevation angle and azimuth angle of the first acoustic signal and elevation angle and azimuth angle of the second acoustic signal.

2. The system according to claim 1, further comprising a processor configured to scan a range of start time differences between the start time of a broadcast of the first acoustic signal and the start time of a broadcast of the second acoustic signal so that the range of start time differences includes a time difference for which the first acoustic signal and the second acoustic signal arrive substantially simultaneously at the mixing zone.

3. The system according to claim 1, further comprising hardware or software or both, configured to control a phase of the first acoustic signal or a phase of the second acoustic signal, or both, such that received signals from the interaction of the first acoustic signal and the second acoustic signal have opposite polarity.

4. The system according to claim 3, wherein the received signals from the interaction of the first acoustic signal and the second acoustic signal having opposite polarities are combined to enhance the signal generated by the non-linear interaction over noise or signals originating from a linear interaction or both.

5. The system according to claim 1, wherein at least a portion of the detected signal generated by the non-linear interaction is proportional to a product of amplitudes of the first acoustic signal and the second acoustic signal.

6. The system according to claim 1, further comprising a time variant band-pass filtering device configured to apply a time-variant frequency band-pass filter to the detected signal so as to keep a narrow frequency bandwidth around an expected frequency bandwidth of the signal generated by non-linear interaction, the narrow frequency bandwidth being selected around the difference between the first frequency and the second frequency.

7. The system according to claim 1, wherein:
    the first acoustic signal comprises a first plurality of pulses arranged as a time sequence, the first plurality of pulses being separated in time, each pulse comprising a first modulated signal at a central frequency, wherein central frequencies of two consecutive pulses are different;
    the second acoustic signal comprises a second plurality of pulses arranged as a time sequence, the second plurality of pulses being separated in time, wherein a separation in time between centers of two consecutive pulses is the same as a separation in time between centers of two corresponding pulses in the first plurality of pulses, wherein a start time difference is provided between a start time of a broadcast of the second plurality of pulses and a start time of a broadcast of the first plurality of pulses, wherein each pulse comprises a second modulated signal, and wherein a central frequency of the second modulated signal within each pulse in the second plurality of pulses is a selected fraction of the central frequency of the first modulated signal within each corresponding pulse in the first plurality of pulses; and
    the start time difference is controlled such that the first acoustic signal and the second acoustic signal intersect in the mixing zone.

8. The system according to claim 7, wherein a separation in time between centers of two consecutive pulses in the first plurality of pulses is greater than a time duration of each pulse.

9. The system according to claim 7, further comprising a processor configured to correlate the detected signal with a template signal comprising a plurality of pulses, the plurality of pulses being arranged in a time sequence and separated in time, wherein a separation in time between centers of two consecutive pulses is the same as the separation in time between centers of two consecutive pulses in the first plurality of pulses, wherein each pulse in the plurality of pulses comprises a modulated signal having a central frequency that is equal to a difference between a central frequency of the first modulated signal and a central frequency of the second modulated signal in each corresponding pulse of the first plurality of pulses and the second plurality of pulses, to obtain a correlated signal containing the signal generated by non-linear interaction in the non-linear mixing zone.

10. The system according claim 9, further comprising a plurality of receivers configured to receive a plurality of detected signals, wherein the processor is configured to apply multi-dimensional filtering, or time moveout analysis and stacking or both, to the plurality of detected signals that are received by the plurality of receivers.

11. The system of claim 9, wherein the receiver comprises a hydrophone or multi-component detectors, or both, and wherein the detected signal comprises a pressure signal detected by the hydrophone or multi-component signals detected by the multi-component detectors or both.

12. The system of claim 11, wherein the processor is further configured to perform hodogram analysis on the detected signal.

13. The system of claim 12, wherein the processor is further configured to apply a hodogram analysis to the three detected component signals corresponding to vertical shear SV, horizontal shear SH and compressional P signals.

14. The system of claim 11, wherein the processor is further configured to apply multi-dimensional filtering, or time moveout analysis and stacking, or both, to the three detected component signals that are received by the three detectors, or to apply multi-dimensional filtering, or time moveout analysis and stacking, or both, to the pressure signal detected by the hydrophone.

15. The system of claim 11, further comprising a time variant band-pass filtering device configured to apply a time-variant frequency band pass filter to the detected signal so as to keep a narrow frequency bandwidth around an expected frequency bandwidth of the signal generated by non-linear interaction, the narrow frequency bandwidth being selected around the difference between the first frequency and the second frequency.

16. The system of claim 15, wherein the processor is further configured to control the first acoustic source, the second acoustic source and the receiver, and repeat a plurality of times the generating of the first acoustic signal, the generating of the second acoustic signal, the receiving of the detected signal, the applying of the time variant frequency band pass filter, the correlating of the detected signal with the template signal, the applying of the hodogram analysis, and the combining of signals to improve signal to noise ratio.

17. The system of claim 15, wherein the processor is further configured to vary the start time difference and repeat a plurality of times the generating of the first acoustic signal, the generating of the second acoustic signal, the receiving of the detected signal, the applying of the time variant frequency band pass filter, the correlating of the detected signal with the template signal, and the applying of the hodogram analysis for each of three detected signals to separate different propagation signal modes including compressional mode P, vertical shear mode SV and horizontal shear mode SH.

18. The system of claim 15, wherein the processor is further configured to vary the start time difference and repeat a plurality of times the generating of the first signal, the generating of the second signal, the receiving of the detected signal, the applying of the time variant frequency band pass filter, and the correlating of the signal detected by a hydrophone with the template signal.

19. The system according to claim 15, wherein the processor is further configured to control the first acoustic source, the second acoustic source and the receiver to scan a plurality of azimuth and elevation angles of the first acoustic signal, a plurality of azimuth and elevation angles of the second acoustic signal, or a position of the receiver, and repeating a plurality of times the generating of the first acoustic signal, the generating of the second acoustic signal, the receiving of the detected signal, the applying of the time-variant frequency band pass filter to obtain a filtered signal, the correlating of the filtered signal with the template signal, and the applying of the hodogram analysis on the three detected component signals to separate the component signals to different propagation signal modes including compressional mode P, vertical shear mode SV and horizontal shear mode SH.

20. The system according to claim 19, wherein the processor is further configured to repeat varying the start time difference between the start time of a broadcast of the first acoustic signal and the start time of a broadcast of the second acoustic signal, to repeat varying the frequency ratio between the first frequency and the second frequency, and to repeat scanning the plurality of azimuth and elevation angles of the first acoustic signal, the plurality of azimuth and elevation angles of the second acoustic signal, and the position of the receiver to obtain a plurality of signal measurements.

21. The system according to claim 20, further comprising a storage device in communication with the processor, the storage device being configured to store the obtained plurality of signal measurements.

22. A method of investigating rock formation outside a borehole comprising:
  generating, by a first acoustic source, a first signal at a first frequency;
  generating, by a second acoustic source, a second signal at a second frequency;
  wherein the first acoustic source and the second acoustic source are arranged and positioned within the borehole and are controllable such that the first and the second acoustic signals intersect in an intersection volume outside the borehole and a start time difference is provided between the second acoustic signal and the first acoustic signal;
  receiving, by a receiver, a detected signal returning to the borehole having a frequency equal to a difference between the first frequency and the second frequency, the detected signal being generated by a non-linear mixing process from the first acoustic signal and the second acoustic signal in a non-linear mixing zone within the intersection volume; and
  recording the detected signal and storing the detected signal in a storage device and recording measurement parameters including a position of the first acoustic source, a position of the second acoustic source, a position of the receiver, elevation angle and azimuth angle of the first acoustic signal and elevation angle and azimuth angle of the second acoustic signal.

23. The method according to claim 22, further comprising scanning a range of start time differences between the start time of a broadcast of the first acoustic signal and the start time of a broadcast of the second acoustic signal so that the range of start time differences includes a time difference for which the first acoustic signal and the second acoustic signal arrive substantially simultaneously at the center of the mixing zone.

24. The method according to claim 22, further comprising controlling a phase of the first acoustic signal or a phase of the second acoustic signal, or both such that received signals from the interaction of the first acoustic signal and the second acoustic signal have opposite polarity.

25. The method according to claim 24, further comprising combining received signals from the interaction of the first acoustic signal and the second acoustic signal having opposite polarities to enhance the signal generated by the non-linear interaction over noise or signals originating from linear interaction, or both.

26. The method according to claim 22, wherein at least a portion of the detected signal generated by the non-linear interaction is proportional to a product of amplitudes of the first acoustic signal and the second acoustic signal.

27. The method according to claim 22, further comprising applying, by a time variant band-pass filter, a time-variant frequency band-pass filter to the detected signal so as to keep a narrow frequency bandwidth around an expected frequency bandwidth of the signal generated by non-linear interaction, the narrow frequency bandwidth being selected around the difference between the first frequency and the second frequency.

28. The method according to claim 22, wherein:
generating the first acoustic signal comprises generating a first plurality of pulses arranged as a time sequence, the first plurality of pulses being separated in time, each pulse comprising a first modulated signal at a central frequency, wherein central frequencies of two consecutive pulses are different;
generating the second acoustic signal comprises generating a second plurality of pulses arranged as a time sequence, the second plurality of pulses being separated in time, wherein a separation in time between centers of two consecutive pulses is the same as a separation in time between centers of two corresponding pulses in the first plurality of pulses, wherein a start time difference is provided between a start time of a broadcast of the second plurality of pulses and a start time of a broadcast of the first plurality of pulses, wherein each pulse comprises a second modulated signal, and wherein a central frequency of the second modulated signal within each pulse in the second plurality of pulses is a selected fraction of the central frequency of the first modulated signal within each corresponding pulse in the first plurality of pulses; and
the start time difference is controlled such that the first acoustic signal and the second acoustic signal intersect in the mixing zone.

29. The method according to claim 28, wherein a separation in time between centers of two consecutive pulses in the first plurality of pulses is greater than a time duration of each pulse.

30. The method according to claim 28, further comprising correlating, by a processor, the detected signal with a template signal comprising a plurality of pulses, the plurality of pulses being arranged in a time sequence and separated in time, wherein a separation in time between centers of two consecutive pulses is the same as the separation in time between centers of two consecutive pulses in the first plurality of pulses, wherein each pulse in the plurality of pulses comprises a modulated signal having a central frequency that is equal to a difference between a central frequency of the first modulated signal and a central frequency of the second modulated signal in each corresponding pulse of the first plurality of pulses and the second plurality of pulses, to obtain a correlated signal containing the signal generated by non-linear interaction in the non-linear mixing zone.

31. The method according claim 30, further comprising receiving a plurality of detected signals at a plurality of receivers and applying, by the processor, multi-dimensional filtering, or time moveout analysis and stacking, or both, to the plurality of detected signals that are received by the plurality of receivers.

32. The method according to claim 30, further comprising detecting a pressure signal by a hydrophone or detecting multi-component signals by multi-component detectors, or both.

33. The method according to claim 30, further comprising detecting each of three components signals of the received signal by each of three detectors of the receiver.

34. The method according to claim 33, further comprising performing, by the processor, hodogram analysis on the detected signal.

35. The method according to claim 34, wherein performing hodogram analysis comprises applying a hodogram analysis to the three detected component signals corresponding to vertical shear SV, horizontal shear SH and compressional P signals.

36. The method according to claim 35, further comprising applying multi-dimensional filtering, or time moveout analysis and stacking, or both, to the three detected component signals that are received by the three detectors, or applying multi-dimensional filtering, or time moveout analysis and stacking, or both, to the pressure signal detected by the hydrophone.

37. The method according to claim 35, applying a time variant frequency band pass filter to the detected signal so as to keep a narrow frequency bandwidth around an expected frequency bandwidth of the signal generated by non-linear interaction, the narrow frequency bandwidth being selected around the difference between the first frequency and the second frequency.

38. The method according claim 37, further comprising repeating a plurality of times the generating of the first acoustic signal, the generating of the second acoustic signal, the receiving of the detected signal, the applying of the time variant frequency band pass filter, the correlating of the detected signal with the template signal, the applying of the hodogram analysis, and the combining of signals to improve signal to noise ratio.

39. The method according claim 37 further comprising varying the start time difference and repeating a plurality of times the generating of the first acoustic signal, the generating of the second acoustic signal, the receiving of the detected signal, the applying of the time variant frequency band pass filter, the correlating of the detected signal with the template signal, and the applying of the hodogram analysis for each of three detected signals to separate different propagation signal modes including compressional mode P, vertical shear mode SV and horizontal shear mode SH.

40. The method according to claim 39, varying the start time difference and repeating a plurality of times the generating of the first signal, the generating of the second signal, the receiving of the detected signal, and the applying of the time variant frequency band pass filter, and the correlating of the signal detected by the hydrophone with the template signal.

41. The method of claim 33, further comprising scanning a plurality of azimuth and elevation angles of the first acoustic signal, a plurality of azimuth and elevation angles of the second acoustic signal, or a position of the receiver, and repeating a plurality of times the generating of the first acoustic signal, the generating of the second acoustic signal, the receiving of the detected signal, the applying of the time variant frequency band pass filter to obtain a filtered signal, the correlating of the filtered signal with the template signal, and the applying of the hodogram analysis on the three detected component signals to separate the component signals to different propagation signal modes including compressional mode P, vertical shear mode SV and horizontal shear mode SH.

42. The method according to claim 41, further comprising repeating the varying the start time difference between the start time of a broadcast of the first acoustic signal and the start time of a broadcast of the second acoustic signal, and repeating the varying the frequency ratio between the first frequency and the second frequency, and repeating the scanning the plurality of azimuth and elevation angles of the first acoustic signal, the plurality of azimuth and elevation angles of the second acoustic signal, and the position of the receiver to obtain a plurality of signal measurements.

43. The method according to claim 42, further comprising storing in a storage device in communication with the processor, the obtained plurality of signal measurements.

* * * * *